US008728983B2

(12) United States Patent
Lowe et al.

(10) Patent No.: US 8,728,983 B2
(45) Date of Patent: May 20, 2014

(54) PHAGE DISPLAY VECTOR

(75) Inventors: Peter Lowe, Droisy (FR); Sven Berger, Poisy (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 50 days.

(21) Appl. No.: 13/510,148

(22) PCT Filed: Nov. 18, 2010

(86) PCT No.: PCT/EP2010/067722
§ 371 (c)(1), (2), (4) Date: Aug. 3, 2012

(87) PCT Pub. No.: WO2011/061244
PCT Pub. Date: May 26, 2011

(65) Prior Publication Data

US 2012/0322678 A1 Dec. 20, 2012

(30) Foreign Application Priority Data

Nov. 18, 2009 (EP) .................................... 09306113

(51) Int. Cl.
*C40B 40/08* (2006.01)

(52) U.S. Cl.
USPC ........................................................... 506/17

(58) Field of Classification Search
None
See application file for complete search history.

(56) References Cited

U.S. PATENT DOCUMENTS

| | | | |
|---|---|---|---|
| 5,849,500 | A | 12/1998 | Breitling et al. |
| 6,057,098 | A | 5/2000 | Buechler et al. |
| 2005/0147962 | A1 | 7/2005 | Wagstrom et al. |
| 2006/0068421 | A1 | 3/2006 | Gray et al. |

FOREIGN PATENT DOCUMENTS

| | | | |
|---|---|---|---|
| WO | WO 92/01047 | A1 | 1/1992 |
| WO | WO 92/06204 | A1 | 4/1992 |
| WO | WO 93/01288 | A1 | 1/1993 |
| WO | WO 01/31065 | A1 | 5/2001 |

OTHER PUBLICATIONS pComb3 vector Creative Biogene Biotechnology downloaded Dec. 20, 2013 from http://www.creative-biogene.com/pComb3-vector-VPT4010-1232906-73.html=4029 bp w/o Ab insert.*

International Search Report issued in PCT/EP2010/067722, mailed on Apr. 19, 2011.

Abraham et al., "Screening and kinetic analysis of recombinant anti-CEA antibody fragments", J. Immunol Methods, 1995, vol. 183, pp. 119-125.

Barbas III et al., "Assembly of combinatorial antibody libraries on phage surfaces: The gene III site", Proc. Natl. Acad. Sci. USA, vol. 88, pp. 7978-7982, 1991.

(Continued)

*Primary Examiner* — Christian Boesen

(74) *Attorney, Agent, or Firm* — Birch, Stewart, Kolasch & Birch, LLP

(57) ABSTRACT

The invention relates to a minimized phage display vector comprising at least a cloning cassette, a phage display cassette and a bacterial cassette, said cloning cassette comprising a nucleic acid sequence encoding a polypeptide corresponding at least to the intra-domain loop of a constant domain of an antibody. It also relates to their uses for the production of libraries of phages, each phage expressing on its surface a binding protein to be screened for its capacity to bind a binding partner.

18 Claims, 13 Drawing Sheets

Figure 1:
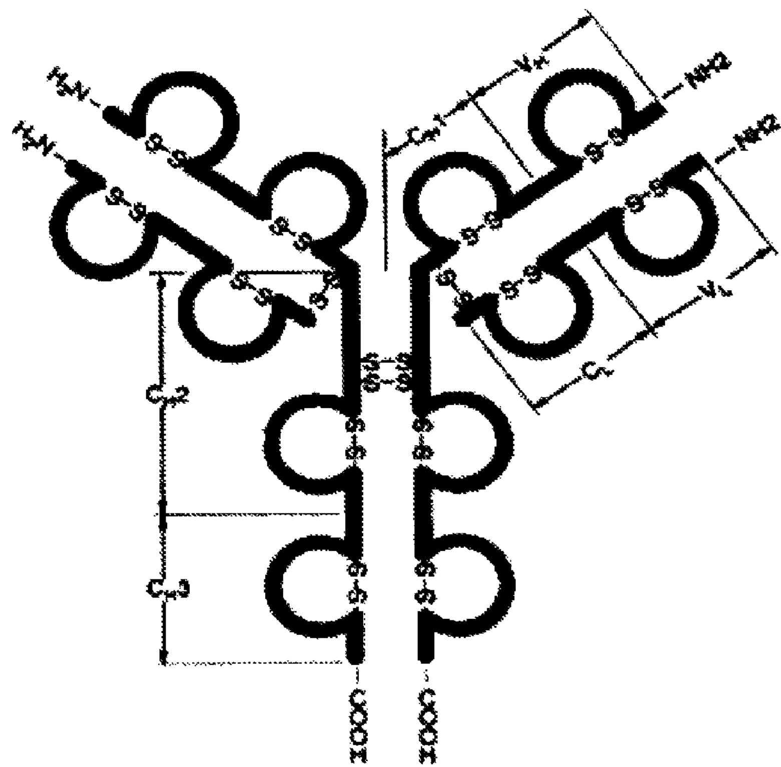

Lac operator
-35
-10
Shine-Dalgarno
pelB
HindIII
SfiI
NcoI
MfeI
Linker peptide
SalI
MluI
CK Domain
6 His tag
Amber STOP
RNA II
pMB1 ori
-35 Signal RNA I
-10 Signal RNA I
RNA I
-10 Signal RNA II
-35 Signal RNA II
pPL31
3158 bp
g3p C-ter
EcoRI
EcoRI
M13 ori region
M13 ori
catR
EcoRI
MfeI
Packaging signal
ApaI
-10 Signal
-35 Signal

(56) References Cited

OTHER PUBLICATIONS

Bes et al., "Efficient CD4 binding and immunosuppressive properties of the 13B8.2 monoclonal antibody are displayed by its CDR-H1-derived peptide CB1", FEBS Letters, vol. 508, 2001, pp. 67-74.
Bes et al.,"PIN-bodies: A new class of antibody-like proteins with CD4 specificity derived from the protein inhibitor of neuronal nitric oxide synthase", Biochemical and Biophysical Research Communications, vol. 343, 2006, pp. 334-344.
Breitling et al., "A surface expression vector for antibody screening", Gene, vol. 104, 1991, pp. 147-153.
Burton et al., "A large array of human monoclonal antibodies to type 1 human immunodeficiency virus from combinatorial libraries of asymptomatic seropositive individuals", Proc. Natl. Acad. Sci, USA, vol. 88, pp. 1034-10137, 1991, Medical Sciences.
Clackson et al., "Making antibody fragements using phage display libraries", Letters to Nature, vol. 352, pp. 624-628.
Kohl et al., "Designed to be stable: Crystal structure of a consensus ankyrin repeat protein", PNAS, vol. 100, No. 4, 2003, pp. 1700-1705.
Kohler, "Continuous cultures of fused cells secreting antibody of predefined specificity", Nature, vol. 256, 1975 pp. 495-497.
McCafferty et al., "Phage antibodies:filamentous phage displaying antibody variable domains", Nature, vol. 348, 1990, pp. 552-554.
Pavoni et al., "New display vector reduces biological bias for expression of antibodies in *E. coli*," Gene, vol. 391, 2007, pp. 120-129.
Siguret et al. "Effect of Plasmid Size on Transformation Efficiency by Electroporation of *Escherichia coli* DH5α" Biotechniques, vol. 16, 1994, pp. 422-426.
Skerra, "Anticalins: a new class of engineered ligand-binding proteins with antibody-like properties", Reviews in Molecular Biotechnology, vol. 74, No. 4, 2001, pp. 257-275.
Skerra, "Engineered protein scaffolds for molecular recognition" Journal of Molecular Recognition, vol. 13, 2000, pp. 167-187.
Smith, "Filamentous Fusion Phage: Novel Experssion Vectors That Display Cloned Antigens on the Virion Surface", Science, vol. 228, 1985, pp. 1315-1317.
Tanaka et al., "Functional display and expression of chicken cystatin using a phagemid system", Biochem Biophys Res Commun. 1995, vol. 214, pp. 389-395.
Harlow; Lane: "Antibodies: A laboratory Manual", 1998, Cold Spring Harbor Laboratory, pp. 726.
Hoogenboom et al., "Multi-subunit proteins on the surface of filamentous phage: methodologies for displaying antibody (FAB) heavy and light chains", Nucleic Acids Research, vol. 19, No. 15, 1991, pp. 4133-4137.

* cited by examiner

```
                            10        20        30        40        50        60        70        80        90        100
                    ....|....|....|....|....|....|....|....|....|....|....|....|....|....|....|....|....|....|....|....|....|..
J00241|IGKC*01      RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID 90)
M11736|IGKC*02      RTVAAPSVFIFPPSDEQLKSGTASVVCLLNNFYPREAKVQWKVDNALQSGNSQESVTEQESKDSTYSLSSTLTLSKADYEKHKVYAGEVTHQGLSSPVTKSFNRGEC (SEQ ID 91)
M11737|IGKC*03      RTVAAPSVFIFPPSDEQLKSGTASVVCLLNNFYPREAKVQRKVDNALQSGNSQESVTEQESKDSTYSLSSTLTLSKADYEKHKVYACEVTHQGLSSPVTKSFNRGEC (SEQ ID 92)
AF017732|IGKC*04    RTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC (SEQ ID 93)
AF113887|IGKC*05    RTVAAPSVFIFPPSDEQLKSGTASVVCLLNNFYPREAKVQWKVDNALQSGNSQESVTEQDSKDSTYSLSNTLTLSKADYEKHKVYACEVTHQGLSSPVTKSFNRGEC (SEQ ID 94)
```

Figure 2

```
                          10        20        30        40        50        60        70        80        90        100
                    ....|....|....|....|....|....|....|....|....|....|....|....|....|....|....|....|....|....|....|....|....|.
X51755|IGLC1*0      QPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS (SEQ ID 95)
J00253|IGLC2*0      QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID 96)
X06875|IGLC2*0      QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID 97)
K01326|IGLC3*0      QPKAAPSVTLFPPSSEELQANKATLVCLISDFYPGPVTVAWKADSSPVKAGVETTTPSKQSNNKYAASSYLSLTPEQWKSHKSYSCQVTHEGSTVEKTVAPTECS (SEQ ID 98)
X06876|IGLC3*0      QPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPTECS (SEQ ID 99)
D87017|IGLC3*0      QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID 100)
J03011|IGLC6*0      QPKAAPSVTLFPPSSEELQANKATLVCLISDFYPGAVKVAWKADGSPVNTGVETTTPSKQSNNKYAASSYLSLTPEQWKSHRSYSCQVTHEGSTVEKTVAPAECS (SEQ ID 101)
X51755|IGLC7*0      QPKAAPSVTLFPPSSEELQANKATLVCLVSDFYPGAVTVAWKADGSPVKVGVETTKPSKQSNNKYAASSYLSLTPEQWKSHRSYSCRVTHEGSTVEKTVAPAECS (SEQ ID 102)
M61771|IGLC7*0      QPKAAPSVTLFPPSSEELQANKATLVCLVSDFYPGAVTVAWKADGSPVKVGVETTKPSKQSNNKYAASSYLSLTPEQWKSHRSYSCRVTHEGSTVEKTVAPAECS (SEQ ID 103)
```

Figure 3

```
                       10        20        30        40        50        60        70        80        90
                ....|....|....|....|....|....|....|....|....|....|....|....|....|....|....|....|....|....|...
J00228|IGHG1*0  STKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV  (SEQ ID 104)
Z17370|IGHG1*0  STKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV  (SEQ ID 105)
J00230|IGHG2*0  STKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV  (SEQ ID 106)
AJ250170|IGHG2  STKGPSVFPLAPCSRSTSESTAALGCLVKDYFPEPVTVSWNSGALTSGVHTFPAVLQSSGLYSLSSVVTVTSSNFGTQTYTCNVDHKPSNTKVDKTV  (SEQ ID 107)
AF449616|IGHG2  STKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV  (SEQ ID 108)
AF449617|IGHG2  STKGPSVFPLAPCSRSTSESTAALGCLVKDYFPEPVTVSWNSGALTSGVHTFPAVLQSSGLYSLSSVVTVPSSSLGTQTYTCNVDHKPSNTKVDKTV  (SEQ ID 109)
AF449618|IGHG2  STKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV  (SEQ ID 110)
AL928742|IGHG2  STKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV  (SEQ ID 111)
M12958|IGHG3*0  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 112)
X16110|IGHG3*0  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 113)
X99549|IGHG3*0  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 114)
AJ390236|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 115)
AJ390237|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 116)
AJ390238|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 117)
AJ390241|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 118)
AJ390242|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 119)
AJ390246|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 120)
AJ390247|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 121)
AJ390252|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 122)
AJ390244|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 123)
AJ390254|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 124)
AJ390260|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 125)
AJ390262|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 126)
AJ390272|IGHG3  STKGPSVFPLAPCSRSTSGGTAALGCLVKDYFPEPVTVSWNSGALTSGVHTFPAVLQSSGLYSLSSVVTVPSSNFGTQTYTCNVNHKPSNTKVDKRV  (SEQ ID 127)
AJ390276|IGHG3  STKGPSVFPLAPCSRSTSGGTAALGCLVKDYFPEPVTVSWNSGALTSGVHTFPAVLQYSGLYSLSSVVTVPSSSLGTQTYTCNVNHKPSNTKVDKRV  (SEQ ID 128)
AJ390279|IGHG3  STKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV  (SEQ ID 129)
K01316|IGHG4*0  STKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV  (SEQ ID 130)
AL928742|IGHG4  STKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV  (SEQ ID 131)
```

Figure 4

PHAGE DISPLAY VECTOR

The present invention concerns the domain of monoclonal antibodies. More particularly, it relates to small size vectors and their uses for the production of libraries of phages, each phage expressing on its surface a binding protein to be screened for its capacity to bind a binding partner.

The phage display method is a technology used for studying interactions of proteins. This technology is based on expressing on the surface of a phage the binding protein of interest and selecting said binding protein on its capacity to form a complex with a binding partner. The principle of this method relies on the genetic recombination of the phage genome: a sequence encoding a binding protein of interest is inserted into said phage genome. The sequence insertion is localized next to a gene encoding a protein forming the coat protein complex of the phage. Said coat is composed of different proteins, such as for example pIII and pVIII proteins which are the most commonly used. The insertion of a sequence of interest next to the gene encoding these proteins enables the fusion of the binding protein of interest to the coat protein of the phage. The recombinant phage then infects bacteria, and its genome is replicated. The expression of the recombinant phagic genome leads to the production of phages expressing on their surface the binding protein to be screened. During the steps of screening, different proteins or molecules, referred to as binding partners, are brought into contact with said protein of interest. When a complex is formed between the binding protein on the surface of the phage and a binding partner, the complex is purified and the nucleotidic sequence encoding the binding protein of interest can then be determined from the recombinant phagic genome.

The principle of phage display dates from 1985 [Smith, G. P., 1985, Science 228, 1315-1317] with the application of this technology for the selection of antibody fragments in combination with helper phage and phagemid vectors [McCafferty, J. et al., 1990, Nature 348, 552-554], [Barbas, C. F. et al., 1991, Proc. Natl. Acad. Sci. U.S.A 88, 7978-7982], [Breitling, F. et al., 1991, *Gene* 104, 147-153], [Burton, D. R. et al., 1991, *Proc. Natl. Acad. Sci. U.S.A* 88, 10134-10137], [Clackson, T. et al., 1991, *Nature* 352, 624-628], [Hoogenboom, H. R. et al., 1991, *Nucleic Acids Res.* 19, 4133-4137]. The phage display method combines the use of phagemid vectors, also called phage display vectors and helper phages for the generation of libraries of phages expressing on their surface a binding protein of interest. Phage display vectors comprise the sequence encoding the binding protein of interest and phagic sequences, especially the sequence encoding the coat protein to be fused with the binding protein of interest. Phage display vectors are also constituted of different functional sequences for the replication of the phagic genome or the maintenance of the vector in the host cell. The phage display vectors do not contain the whole phagic genome, this is why this method is combined with the use of a helper phage for the production of phages expressing binding proteins on their surface. The helper phage enables the replication and packaging of the phagic genome on the phage display vector by complementing proteins from the complete phage genome absent in the phage display vector.

It must be reminded here that, in contrast to classical phage vectors comprising the whole of the bacteriophage M13 genome, phage display vectors, also referred as phagemid vectors, comprise only a small portion of the M13 genome including a fraction of the gene III and the M13 intergenic region.

By example, such phage vectors are classically large vectors (generally more than 6000 base pairs) and can consist of the vectors M13IX30, M13IX11, M13IX34, M13IX13 or M13IX60 described in the patent application WO92/06204 or any derived phage vectors such as the vector 668-4 used in a method for generating polyvalent display library described in the U.S. Pat. No. 6,057,098.

The first phagemid vectors pCANTAB [Abraham, R. et al., 1995, J. Immunol. Methods 183, 119-125], [Tanaka, A. S. et al., 1995, Biochem. Biophys. Res. Commun. 214, 389-395], pHEN [Hoogenboom, H. R. et al., 1991, *Nucleic Acids Res.* 19, 4133-4137], [WO 92/01047], pCOMB [Barbas, C. F. et al., 1991, *Proc. Natl. Acad. Sci. U.S.A* 88, 7978-7982], [Burton, D. R. et al., 1991, *Proc. Natl. Acad. Sci. U.S.A.* 88, 10134-10137], were constructed from cloning and expression vectors available at the time using the molecular biological tools available. Since this time little optimisation has been applied to the phagemid vector, a rare example being pKM19 [Pavoni, E. et al., 2007, *Gene* 391, 120-129], the construction of which takes into account the advantages of an optimised promoter and use of the C-terminal domain of the gene III product of the bacteriophage M13 [Barbas, C. F. et al., 1991, Proc. Natl. Acad. Sci. U.S.A. 88, 7978-7982].

The present invention relates to a phage display vector comprising a cloning cassette, a phage display cassette and a bacterial cassette and its use for the generation of a library of phages, each member of the library expressing on its surface a binding protein. As it will be apparent in the following description, each of the three cassettes is optimized to generate a functional vector suitable for the phage display of binding proteins.

To this date, if the technology seems to be robust, there is still an insufficiency regarding the expression level of the protein of interest. Another disadvantage of this technology as used until now is the detection and the purification of the selected binding proteins.

The present invention proposes to solve these problems and describes for the first time a novel and non obvious optimised phage display vector.

In a first aspect, the present invention relates to a minimized phage display vector comprising at least a cloning cassette, a phage display cassette and a bacterial cassette, said cloning cassette comprising a nucleic acid sequence encoding a polypeptide corresponding at least to the intra-domain loop of a constant domain of an antibody.

In the present specification, for the avoidance of doubt, a "cassette" should be considered as a DNA fragment comprising specific nucleic acid sequences with specific biological and/or biochemical activity(ies). The expressions "cassette", "gene cassette" or "DNA cassettes" could be used interchangeably and have the same meaning.

A cloning cassette should be considered as a cassette having an activity in the cloning of a gene. It thus contains the required nucleic acid sequences for the regulation and the expression of one or several gene(s) of interest to be cloned. It comprises at least a nucleic acid sequence encoding a promoter, a stop codon, and a cloning site useful for the introduction of the gene(s) of interest, each of these components being operably linked with each other.

The term "operably linked" or "operably inserted" means that the regulatory sequences necessary for expression of the coding sequence are placed in a nucleic acid molecule in the appropriate position relative to the coding sequence so as to enable expression of the coding sequence. By way of example, a promoter is operably linked with a coding sequence when the promoter is capable of controlling the transcription or expression of that coding sequence.

A phage display cassette should be considered as a cassette having an activity in the phage display method, more precisely for the production of a library of phages expressing on their surface the protein(s) of interest. It comprises at least a nucleic acid sequence encoding a phagic replication origin, in order to a) be able to replicate the replication vector comprising the phagic origin as ssDNA carried by said vector, and b) produce recombinant phages with the complementation of a functional phage genome.

A bacterial cassette should be considered as a cassette containing the required sequence(s) for the multiplication and maintenance of the vector in the bacterial host cell. A bacterial cassette would thus comprise principally at least nucleic acid sequences encoding a replication origin and a selective marker.

More details concerning the composition of those cassettes will be found below.

Nevertheless, it must be understood that any modification obvious for the man skilled in the art should be considered as encompassed by the present invention.

The term "nucleic acid" refers to desoxyribonucleotides or ribonucleotides and polymers thereof ("polynucleotides") in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "nucleic acid", "nucleic acid sequence", "nucleotide sequence" or "nucleotide molecule" may also be used interchangeably with gene, cDNA, DNA and RNA encoded by a gene. Thus, the cloning cassette according to the invention comprises a nucleic acid sequence encoding at least a polypeptide corresponding to the intra-domain loop of a constant domain of an antibody. In a preferred embodiment of the invention, said nucleic acid sequence is inserted into the cloning cassette next to the cloning site. This preferred insertion localization allows the obtention, in the case of the insertion of a (full length) constant domain, of a single chain antibody composed of an scFv antibody fragment and a constant domain. It has been shown that the presence of the constant domain enables an improved functional expression of the protein of interest, i.e. the single chain antibody. The constant domain also enables improved detection and purification of the binding protein produced from the nucleic acid sequences inserted in the phage display vector.

The terms "antibody", "antibodies" or "immunoglobulin" are used interchangeably in the broadest sense and include monoclonal antibodies (e.g., full length or intact monoclonal antibodies), polyclonal antibodies, multivalent antibodies or multispecific antibodies (e.g., bispecific antibodies so long as they exhibit the desired bio logical activity).

More particularly, such molecule consists of a glycoprotein comprising at least two heavy (H) chains and two light (L) chains inter-connected by disulfide bonds. Each heavy chain is comprised of a heavy chain variable region (or domain) (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region comprises one domain, CL. The VH and VL regions can be further subdivided into regions of hypervariability, termed complementarity determining region (CDR), interspersed with regions that are more conserved, termed framework region (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

They may also include certain antibody fragments, as described in greater detail herein, thereof which exhibit the desired binding specificity and affinity, regardless of the source or immunoglobulin type (i.e., IgG, IgE, IgM, IgA, etc.).

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

Those skilled in the art will appreciate that heavy chains are classified as gamma, mu, alpha, delta, or epsilon, ($\gamma, \mu, \alpha, \delta, \epsilon$) with some subclasses among them (e.g., .gamma.1-.gamma.4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization.

Light chains are classified as either kappa or lambda ($\kappa, \lambda$).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3, or CH4 in the case of IgM and IgE) confer important biological properties such as secretion, transplacental mobility, Fc receptor binding, complement binding, and the like. By convention the numbering of the constant region domains increases as they become more distal from the antigen binding site or amino-terminus of the antibody.

By the expression "constant domain" of an antibody it understood the antibody region without any variability from one antibody to another of the same isotype and allotype, compared to the variable regions of an antibody which contain all the diverse sequences capable of recognizing epitopes of antigens.

Into each of these constant domains, i.e. CL, CH1, CH2, CH3 and CH4, a disulphide bond is forming a loop of about 60 amino acids. In the present specification, said loop will be called intra-domain loop.

In the preferred case of a human IgG CH1, there exist 28 different possible gamma heavy chains, each possessing a constant domain CH1 consisting of a polypeptide of 97 amino-acids (SEQ ID Nos. 104 to 131). Each of these 28 domains presents a residue cysteine in position 26 and another one in position 82 forming a disulfide bridge with, as a result, the formation of a disulphide bond between these two cysteines, thus forming an intra-domain loop.

In a particular embodiment of the invention, the cloning cassette comprises a nucleic acid sequence encoding at least a polypeptide corresponding to the intra-domain loop of a heavy chain constant domain of an antibody.

More particularly, a preferred intra-domain loop for the heavy chain is the CH1 intra-domain loop composed of the polypeptide comprised between the Cysteine in position 26 and the cysteine in position 82.

In a more preferred embodiment, the cloning cassette comprises a nucleic acid sequence encoding at least a polypeptide corresponding to a heavy chain constant domain of an antibody.

In a more preferred embodiment, the heavy chain constant domain of an antibody is the CH1 heavy chain constant domain of an antibody.

It will be evident, for the man skilled in the art, to define the intra-domain loop of another heavy chain constant domain to be used according to the invention.

In another embodiment of the invention, the cloning cassette comprises a nucleic acid sequence encoding at least a polypeptide corresponding to the intra-domain loop of a light chain constant domain of an antibody.

In humans, there exist 5 different Kappa chains, each of them corresponding to a polypeptide of 107 amino-acids with two Cysteine residues, in position 27 and 87 respectively, forming an intra-domain loop (SEQ ID No. 90 to 94).

More particularly, a preferred intra-domain loop for the Kappa light chain is the intra-domain loop composed of the polypeptide comprised between the Cysteine in position 27 and the cysteine in position 87.

For the human lambda chain, there are 9 distincts forms, each of them corresponding to a polypeptide of 105 amino-acids with two Cysteine residues, in position 27 and 86 respectively, forming an intra-domain loop (SEQ ID No. 95 to 103).

More particularly, a preferred intra-domain loop for the Lambda light chain is the intra-domain loop composed of the polypeptide comprised between the Cysteine in position 27 and the cysteine in position 86.

In another embodiment, the cloning cassette comprises a nucleic acid sequence encoding a polypeptide corresponding at least to a light chain constant domain of an antibody.

In a preferred embodiment of the invention, the constant domain of the cloning cassette is the light chain Kappa constant domain.

The origin of the Kappa constant domain used in the present invention is preferentially human.

In a most preferred embodiment of the invention, said constant domain of said cloning cassette is the light chain Kappa constant domain with the C-terminal cysteine deleted.

Said Kappa constant domain is devoid of C-terminal cysteine in order to prevent the dimerization of single chain antibodies expressed on the surface of the phage, such dimerization being possible between the Kappa constant domains. Indeed, constant domains of heavy and light chains of an antibody assemble by the formation of a disulphide bond between the C-terminal cysteine of the light chain and a non-paired cysteine in the heavy constant domain. The present invention provides binding proteins on the surface of phages. Not removing the C-terminal cysteine of the constant domain would lead to a possible dimerization of single chain antibodies and non representative binding through the effect of avidity.

The removal of the C-terminal cysteine is necessary to prevent said dimerization, and thus applied in order to prevent the miss folding or aggregation of the gIII fusion protein, due to the dimerization of the single chain antibodies.

In another preferred embodiment of the invention, the constant domain of the cloning cassette is the light chain Lambda constant domain.

The origin of the Lambda constant domain used in the present invention is preferentially human.

In a most preferred embodiment of the invention, said constant domain of said cloning cassette is the light chain Lambda constant domain with the cysteine in position 104 (SEQ ID Nos. 95 to 103) deleted. In another embodiment, the C-terminal residues 104 and 105 (Cysteine-Serine) can be deleted (SEQ ID Nos. 95 to 103).

To date the expression of a single chain Fv fused to a single constant domain for the presentation and selection by phage display has not been described.

Another particularly innovative aspect of the invention is the size of the vector.

The transformation efficiency of *E. coli* is the limiting step to generating a high diversity library and vector size is inversely proportional to transformation efficiency [Siguret, V. et al., 1994, Biotechniques 16, 422-426]. Currently described phage display vectors present sizes in the absence of the binding partner variable domains in excess of 3390 base pairs and typically in excess of 4500 bp, with increased vector size, the transformation efficiency will decrease thus reducing the size of the obtained library, or demanding repeated transformation to achieve high diversity.

The sizes of currently described phage display vectors not containing any constant domain are listed as it follows:

| | |
|---|---|
| pCANTAB 5E | 4522 bp |
| pHEN1 | 4523 bp |
| pHEN2 | 4616 bp |

The size of other used M13 phage vectors are also listed hereinafter (see, for example, WO92/06204):

| | |
|---|---|
| M13IX30 | 7445 bp |
| M13IX11 | 7317 bp |
| M13IX34 | 7729 bp |
| M13IX13 | 7557 bp |
| M13IX60 | 8118 bp |

The phage display vector size is inversely proportional to transformation efficiency.

Another goal of the invention is to optimize the efficiency of the transformation of host cells. This technical problem is solved by reducing the size of the vector of the invention while maintaining all the necessary biological activities. Another particular inventive aspect of the invention is based on the removal of non functional nucleotides in and between said three cassettes thus minimizing the phage display vector size and thus optimizing the transformation efficiency. It must be understood, at this stage, that for the man skilled in the art, such a reduction of the size of the phage display vector was not obvious as it was not predictable that the activity of the said minimized phage display vector will be conserved (see example 7). As an illustration of this point, it is mentioned here that phage display vectors exist since the birth of the technology, i.e. since the eighties, and there is no prior art referring to the reduction of the size of said phage display vectors.

The deletion of non-functional nucleotides in the vector enables the generation of a library of smaller vectors and generates less stress on the host cells. The vector is also maintained more easily in the host cells.

The result of these deletions is a novel phage display vector of less than 3300 base pairs including the size of the nucleic acid sequence encoding at least a polypeptide corresponding to the intra-domain loop of a constant domain of an antibody, which is a characteristic of the invention as described above. It is significantly less than the common size observed in the vectors of the prior art which do not include such a nucleic acid sequence encoding a constant domain or an intra-domain loop of such a constant domain (in excess of 4500 base pairs). To facilitate the comparison, we can consider that the size of the phage display vector according to the invention without any nucleic acid sequence encoding at least a polypeptide corresponding to the intra-domain loop of a constant domain of an antibody would be less than 3000 base pairs.

By way of example, can be mentioned the vectors pPL12 and pPL14, 3246 base pairs (corresponding to 2928 base pairs without nucleic acid sequences encoding the polypeptide corresponding to the intradomain loop of an antibody) and pPL22, 3109 base pairs (corresponding to 2751 base pairs without nucleic acid sequences encoding the polypeptide corresponding to the intradomain loop of an antibody). It can also be mentioned the vector pPL31 which comprises 3158 base pairs. It must be understood that these four vectors, clearly illustrated in the following examples, are non limitative examples of vectors according to the invention.

The sequences of these four vectors, pPL12, pPL14, pPL22 and pPL31, are represented in sequences SEQ ID Nos. 1, 5, 7 and 148, respectively.

To date the use of a minimized vector comprising a nucleic acid sequence encoding at least a polypeptide corresponding to the intra-domain loop of a constant domain of an antibody and not exceeding 3300 base pairs has not been neither described nor suggested.

For the avoidance of doubt, the expression “minimized vector” must be understood as a vector having a size of 3300 base pairs or less.

The phage display vector of the invention is used to generate a library of phages expressing on their surface binding proteins to be screened.

A “binding protein” is a peptidic chain having a specific or general affinity with another protein or molecule. Proteins are brought into contact and form a complex when binding is possible. The binding protein of the invention expressed on the surface of a phage can preferably be an antibody, a fragment or derivative of an antibody, a protein or a peptide.

The phage display method can thus be used, in a preferred embodiment of the invention, as a screening method to determine specific antibodies binding new target molecules such as antigens. This technology presents the advantage of selecting specific antibodies or antibody fragments without any step of animal immunization for the generation of said antibodies. The phages expressing the binding proteins of interest are directly generated in bacterial cells.

The nucleic acid sequences inserted into the cloning site of the phage display vector and correspond to the sequences encoding variable chains of an antibody, forming a fragment of an antibody also called scFv, single chain Fv, which will be explained below.

By “functional fragment” of an antibody according to the invention, it is intended to indicate in particular an antibody fragment, such as fragment variable (Fv), scFv (sc for single chain), fragment antigen binding (Fab), $F(ab')_2$, Fab', scFv-Fc fragments or diabodies, or any fragment of which the half-life would have been increased by chemical modification, such as the addition of poly(alkylene) glycol such as poly(ethylene) glycol (“PEGylation”) (pegylated fragments called Fv-PEG, scFv-PEG, Fab-PEG, $F(ab')_2$-PEG or Fab'-PEG) (“PEG” for Poly(Ethylene) Glycol), and, especially, in that it is capable of exerting in a general manner an even partial activity of the antibody from which it is descended.

Preferably, said functional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of that of the antibody from which it is descended. Such a functional fragment will contain at the minimum 5 amino acids, preferably 10, 15, 25, 50 and 100 consecutive amino acids of the sequence of the antibody from which it is descended.

Preferably, these functional fragments will be fragments of Fv, scFv, scFv-Fc type or diabodies, which generally have the same specificity of binding as the antibody from which they are descended. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, or gene synthesis.

A “single chain variable fragment” (scFv) is a fragment of an antibody, as defined above, composed of variable regions of heavy and light chains of antibody, linked together by a binding peptide. These fragments do not exist in a natural state, but have been constructed artificially. The order of the variable regions heavy-light or light-heavy in the single chain variable fragment has no significant effect on the recognition of the binding partner nor expression of the recombinant protein, and thus the order of the variable regions can be considered interchangeable. The binding peptide introduced in cis between the variable regions serves to orient the variable regions in a three dimensional configuration resembling that of a natural antibody. The choice of binding peptide influences the resulting scFv in numerous ways; peptide length effects the formation of monomeric or multimeric scFv compounds. Shorter binding peptides favour the formation of multimeric scFvs as dimmers, trimers or tetramers, longer binding peptides in excess of twelve amino acids favour the formation of monomers. The binding peptide ideally consists of amino acid residues that will not limit the folding or binding of the expressed scFv, the amino acid composition favouring small amino acids which are polar an non ionizable.

A “single chain antibody” is defined as a binding molecule composed of a scFv fragment and a constant domain of an antibody. A single chain antibody thus presents variable regions of one heavy and one light chain containing a binding domain from the heavy or light chain that interacts with an antigen.

By “derivative” of an antibody according to the invention, it is meant a binding protein comprising a protein scaffold and at least one of the CDRs selected from the original antibody in order to maintain the binding capacity. Such compounds are well known by a person skilled in the art and will be described in more detail in the following specification.

More particularly, the antibody, or one of its functional fragments or derivatives, according to the invention is characterized in that said derivative consists of a binding protein comprising a scaffold on which at least one CDR has been grafted for the conservation of the original antibody paratope.

One or several sequences of the 6 CDR sequences described in the invention can be presented on a protein scaffold. In this case, the protein scaffold reproduces the protein backbone with appropriate folding of the grafted CDR(s), thus allowing it (or them) to maintain their antigen binding paratope.

One skilled in the art knows how to select the protein scaffold on which at least one CDR selected from the original antibody could be grafted. More particularly, it is known that, to be selected, such scaffolds should display several features as follow (Skerra A., J. Mol. Recogn., 13, 2000, 167-187):

phylogenetically conserved, robust architecture with a well known three-dimensional molecular organization (such as, for example, crystallography or NMR), small size, no or only low degree of post-translational modifications, easy to produce, express and purify.

Such protein scaffolds can be, but without limitation, structures selected from the group consisting in fibronectin and preferentially the tenth fibronectin type III domain (FNfn10), lipocalin, anticalin (Skerra A., J. Biotechnol., 2001, 74(4): 257-75), the protein Z derivative from the domain B of staphylococcal protein A, thioredoxin A or any protein with repeated domain such as "ankyrin repeat" (Kohl et al., PNAS, 2003, vol. 100, No. 4, 1700-1705), "armadillo repeat", "leucine-rich repeat" or "tetratricopeptide repeat".

A further selection of scaffold derivatives from toxins (such as, for example, scorpion, insect, plant or mollusc toxins) or protein inhibitors of neuronal nitric oxide synthase (PIN) should also be considered.

As a non limitative example of such hybrid constructions, it can has been demonstrated that the insertion of the CDR-H1 (heavy chain) of an anti-CD4 antibody, i.e. the 13B8.2 antibody, into one of the exposed loop of the PIN. The binding properties of the obtained binding protein remain similar to the original antibody (Bes et al., BBRC 343, 2006, 334-344). It can also be mentioned the grafting of the CDR-H3 (heavy chain) of an anti-lyzozyme VHH antibody on a loop of neocarzinostatine (Nicaise et al., 2004).

As above mentioned, such protein scaffolds can comprise from 1 to 6 CDR(s) from the original antibody. In a preferred embodiment, but without limitation, one skilled in the art would select at least a CDR from the heavy chain, said heavy chain being known to be particularly implicated in the antibody specificity. The selection of the CDR(s) of interest will be evident to a person of the art with known methods (BES et al., FEBS letters 508, 2001, 67-74).

As evidence, these examples are not limitative and any other scaffold known or described must be included in the present specification.

According to another aspect, the cloning cassette of the vector according to the invention comprises at least a nucleic acid sequence encoding a promoter and a nucleic acid sequence encoding a signal peptide.

A promoter is a nucleic acid sequence enabling the initiation of the transcription of a gene sequence in a messenger RNA, such transcription being initiated with the binding of the RNA polymerase on said promoter.

The sequence encoding said promoter can be selected, as non limitative examples, from the group consisting of Lac, Tac, Trp, Tet, T7, SP6.

In a preferred embodiment, the promoter of said cloning cassette of the invention is the Lac promoter.

A "signal peptide" is a peptidic chain responsible of the localization of a binding protein of interest after its expression in the cell. The peptide signal sequence is situated next to the sequence encoding said binding protein of interest on the vector. For correct incorporation of the binding protein of interest in an assembled phage capsid containing the phage display vector in a single stranded DNA composition requires targeting of the binding protein of interest to the periplasmic space of the host organism by a peptide signal. The structure of the binding protein of interest requires the formation of disulphide bonds in the case of a single chain antibody. The periplasmic space being an oxidative environment, the structural folding of said single chain antibody can be performed.

The sequence encoding said signal peptide can be selected, as non limitative examples, from the group consisting of sequences encoding pelB, geneIII, phoA, malE, dsbA.

In a preferred embodiment, the signal peptide of said cloning cassette is the pelB signal peptide.

In another aspect, the cloning cassette of the vector according to the invention further comprises a nucleic acid sequence encoding a cloning site.

As used herein, the term "cloning site" refers to a nucleic acid sequence containing a restriction site for restriction endonuclease-mediated cloning by ligation of a nucleic acid sequence containing compatible cohesive or blunt ends, a region of nucleic acid sequence serving as a priming site for PCR-mediated cloning of insert DNA by homology and extension "overlap PCR stitching", or a recombination site for recombinase-mediated insertion of target nucleic acid sequences by recombination-exchange reaction, or mosaic ends for transposon mediated insertion of target nucleic acid sequences, as well as other techniques common in the art.

In a preferred embodiment, the cloning site according to the invention comprises at least two restriction sites.

As non limitative example, it can be mentioned a cloning cassette of sequence SEQ ID No. 2 as a preferred cloning cassette.

The phage produced by the invention, and defined below, presents on its surface a binding protein comprising a light chain and a heavy chain of an antibody, a binding peptide and a constant domain. Two restriction sites may be needed to insert in the vector the sequences encoding the light and heavy chains.

The formation of a single chain antibody composed of variable light and heavy chains with at least a polypeptide corresponding to the intra domain loop of a constant domain antibody is realised thanks to the linkage operated by a binding peptide between the variable light and heavy chains.

The sequence of said binding peptide can be inserted into the vector. It may also be already present in the vectors, such as the pPL12, pPL14, pPL22 and pPL31 vectors non limitatively exemplified in the present invention, wherein additional restriction sites may be required for directed insertion.

The phage display cassette can comprise all or part of a nucleic acid sequence encoding the M13 gene III protein. Nevertheless, nucleic acid sequences encoding the M13 gene VII, VIII or IX protein can also be used.

The M13 gene III protein is a protein from the M13 phage, and is part of the complex forming the capsid of the phage. The gene III protein is located at the distal extremity of the secreted phage, and its quantity in the capsid is not limited to one protein, but can be numbered from several to five gene III proteins. The nucleic acid sequences encoding a binding protein are localized next to the nucleic acid sequence encoding the M13 gene III protein on the vector. Following translation, the binding protein is thus fused to the gene III protein. Regulation of expression levels of the fusion protein from the phage display vector permits the regulation of the number of copies of fusion protein compared to wild type pIII provided by phage genome complementation. Ideally low numbers of fusion proteins will be incorporated in each phage capsid to prevent avidity of the presented binding molecule.

In a preferred embodiment, the vector is characterized in that the phage display cassette comprises a nucleic acid sequence comprising at least the C-terminal domain of M13 gene III protein corresponding to the SEQ ID No. 132 or 133.

Another aspect of the invention is the use of the C-terminal sequence only of the M13 gene III protein. This nucleic acid sequence codes for the part of the protein which is attached to the phage and forms the coat protein complex.

The C-terminal sequence encoding the M13 gene III protein presents the nucleic acid sequence of the wildtype of the M13 gene III protein (SEQ ID No. 133). However, this nucleic acid sequence can be optimized in the present invention with the mutation of a single amino acid from the wild type sequence (S110G) corresponding to a single nucleotide mutation (A328G). The sequence of said C-terminal M13 gene III protein has been optimised by Geneart for expression in *E. coli* and corresponds to SEQ ID No. 132.

In a most preferred embodiment, the phage display cassette comprises an optimized nucleic acid sequence comprising at least the C-terminal domain of M13 gene III protein corresponding to the SEQ ID No. 132.

In another aspect of the invention, the phage display cassette according to the invention comprises a nucleic acid sequence encoding a stop codon, a nucleic acid sequence encoding a phagic replication origin, and a nucleic acid sequence encoding an encapsulation or packaging sequence.

A stop codon is a short sequence constituted of three nucleotides, and responsible for the termination of mRNA translation. The combination of the three nucleotides not coding for any amino acid, the ribosomal translation of the mRNA into a protein ends.

The sequence of the stop codon of the present invention should be localized between the nucleic acid sequence encoding a polypeptide corresponding to the intra domain loop of a constant domain of an antibody and the nucleic acid sequence encoding the M13 gene III protein. The function of the stop codon will depend on the host strains which will be transformed with the phage display vector of the invention, as its interpretation differs according to the chosen cell strain.

In the case of a suppressor strain, the stop codon is recognized by the strain as an amino acid. The translation is thus not interrupted and the product of the translation is a fusion of the gene III protein and the binding molecule expressed on the surface of the phage.

In the case of a non suppressor strain, the stop codon is recognized and the translation is stopped. The product of the translation is thus the binding molecule. Non suppressor strains can be used for the production of the binding molecule alone after the screening and detection of the single chain antibody for complex formation with a binding partner. It can also be used for the analysis of the structure of the single chain antibody without being linked to the gene III protein and being presented on the surface of a phage.

Three stop codons have been described, and are constituted of three nucleotides: the amber stop codon (TAG), the ochre stop codon (TAA) and the opal stop codon (TGA).

In a preferred embodiment, the stop codon of the phage display cassette of the invention is an amber stop codon.

The "origin of replication" in the phage display cassette is a phagic replication origin which can initiate, with complementation of a complete phage genome, the replication of sequences of phagic origin and sequences encoding the binding protein of interest carried on the vector as single stranded DNA for later encapsulation in recombinant phages.

The phagic origin of replication thus facilitates the replication of the vector as a single stranded DNA form that can then be encapsulated into phage particles. Single stranded vector DNA is encapsulated in bacteriophage capsid through complete phage genome complementation.

The nucleic acid sequence of the phagic origin of replication of the invention can be preferably the non wildtype sequence of the M13 phage containing a mutation of a single nucleotide, i.e. the nucleotide G (SEQ ID No. 6) by the nucleotide A (SEQ ID No. 3) in position 529. Said mutation results in more phage particles being produced.

A "packaging signal" is a phagic nucleotidic sequence responsible of the regulation of the packaging of the sequences encoding the binding protein of interest and sequences of phagic origin into a protective and functional capsid. In order to package the genome of the phage containing the nucleic acid sequences encoding the binding protein of interest, the packaging signal needs to be present in the phage display vector of the invention. The phage genome used for complementation is compromised in the packaging signal leading to a preferential packaging of the vector of the invention.

The nucleic acid sequence of the packaging signal of the invention can be the wildtype sequence of the M13 phage but, preferably, contains a mutation of a single nucleotide, i.e. the nucleotide G (SEQ ID No. 6) by the nucleotide A (SEQ ID No. 3) in position 784. Said mutation confers superior soluble recombinant phage and protein of interest than with the M13 wild type packaging signal.

As non limitative examples, it can be mentioned a phage display cassette selected from the group consisting in the phage display cassettes of sequences SEQ ID No. 3, 6 and 149.

In another aspect of the invention, said bacterial cassette of the phage display vector comprises at least a nucleic acid sequence encoding a promoter, a nucleic acid sequence encoding a positive selective marker and a nucleic acid sequence encoding a replication origin.

The bacterial cassette according to the invention comprises a nucleic acid sequence coding for a promoter. Said promoter is responsible for the transcription of the gene encoding the positive selectable marker.

In a preferred embodiment, the promoter of the bacterial cassette can be a beta lactamase promoter.

A "positive selective marker" is a nucleic acid introduced into a vector in order to select for and maintain in culture, transformed bacteria with said vector. Such nucleic acid sequence can be a gene or any alternative regulatory sequence, such as an inhibitory RNA.

In a preferred embodiment, said positive selective marker can be an ampicillin or a chloramphenicol resistance gene.

Host cells presenting a positive success of transformation, i.e. cells in which the vector has been introduced and remains will be able to survive and mutliplicate on a medium containing an antibiotic because of said antibiotic resistance confered by the selective marker gene to the host.

The vector according to the invention can further comprise, if necessary, a nucleic acid sequence encoding a transcription terminator.

A "transcription terminator" is a nucleotidic sequence which ends the RNA polymerase transcription of a gene into mRNA, herein the gene encoding the positive selective marker. The transcription of the nucleic acid sequences encoding the variable regions of the antibody, the constant domain or the intra-domain loop of a constant domain of an antibody and the M13 gene III protein needs to be under the control of the promoter of the cloning cassette. Therefore the transcription of the selective marker needs to be stopped, as it is under the control of the bacterial cassette's promoter.

The nucleic acid sequence of the transcription terminator is preferentially localized in the phage display vector, next to the gene encoding the selectable marker.

In another aspect, the bacterial cassette of the invention comprises a nucleic acid sequence comprising a replication origin. This replication origin enables the vector to replicate in the bacterial host after its transformation.

As non limitative examples, it can be mentioned a bacterial cassette selected from the group consisting in the bacterial cassettes of sequences SEQ ID No. 4, 8 and 150.

According to another preferred embodiment, the invention describes here a minimized phage display vector, named pPL12, which comprises the nucleic acid sequence SEQ ID No. 1.

According to another preferred embodiment, the invention describes here a minimized phage display vector, named pPL14, which comprises the nucleic acid sequence SEQ ID No. 5.

According to another preferred embodiment, the invention describes here a minimized phage display vector, named pPL22, which comprises the nucleic acid sequence SEQ ID No. 7.

According to another preferred embodiment, the invention describes here a minimized phage display vector, named pPL31, which comprises the nucleic acid sequence SEQ ID No. 148.

Another aspect of the invention is a process of engineering a library of minimized phage display vectors according to the invention, said process being characterized in that it comprises the following steps:

a) Inserting the nucleic acid sequences encoding the binding protein in the minimized phage display vector of the invention;

b) Transforming a host cell with said minimized phage display vector.

A "library of phage display vectors" is a collection of vectors according to the invention, or host cells containing said vectors, each of said vectors comprising sequences encoding binding proteins different from one vector to another.

A "host cell" is an organism used for the expression of genes of interest which are localized on vectors of expression. Said vectors are capable of replicating themselves but need biological material of a host for different biological reactions such as replication, transcription and translation. A host cell is thus a cell in which the phage display vector of the invention will replicate and produce, with phage genome complementation, a library of phages expressing on their surface a binding molecule. The step a) of said process of engineering a library of phage display vectors of the invention can be performed with the techniques known in the art, such as restriction digest, homologous recombination, or ligation independent cloning.

The step b) of said process can be performed, as non limitative example, by chemical or heat shock transformation or, in a preferred embodiment, by electroporation.

Another aspect of the invention is a library constituted of minimized phage display vectors obtained from the process of engineering said library of phages as stated above.

In a preferred embodiment, the host cell of step b) can be selected from the group consisting of *E. coli* strains TG1, XL1-Blue, XL1-Blue MRF', K12 ER2738 cells.

In a preferred realization of the invention, the host cell is *E. coli* TG1.

Another aspect of the invention is a process of producing a library of minimized phages, said process comprising the two steps of the process of engineering a library of vectors previously described and an additional step c) of replication, encapsulation and secretion of a phage-binding protein complex by complementation of bacteriophage proteins I-XI.

A "library of phages" is a collection of phages each expressing on their surface different binding proteins from one phage to another. A library of phages can thus be used to screen for a binding protein of interest with a binding partner. The formation of a complex between a phage, the binding protein expressed on its surface and said binding partner will then enable the determination as to which phage express the binding protein of interest. After having selected the complex, the sequences on the vector will be analyzed in order to obtain the exact sequences encoding the binding protein of interest.

The complementation of step c) can be achieved through the addition of replication and packaging inefficient helper phage such as M13KO7, R408, VCSM13 or through transformation in step b) of a host cell capable of expressing the necessary phage proteins to complement the replication and secretion of the phagemid vector.

Another aspect of the invention is a library constituted of phages obtained from the process of producing said library of phages as stated above.

Still another aspect of the inventions is a phage obtained from the process of producing a library of phages as described above, said phage expressing the binding protein of interest on its surface.

The invention also concerns a process of screening for a binding protein of interest specific to a binding partner, comprising the steps of:

a) bringing into contact binding partners with the library of phages according to the invention;

b) selecting the complex formed by the binding protein of interest and the binding partner;

c) extracting the sequences encoding said binding protein of interest from the vector, and d) producing the binding protein of interest.

A binding partner is a synthetic or natural molecule or protein to which an antibody can selectively bind. The binding partner may be a polypeptide, polysaccharide, carbohydrate, nucleic acid, lipid, hapten or other naturally occurring or synthetic compound.

The step a) of said process of screening for a binding protein can be performed by bringing into contact a binding partner with the library of phages expressing said binding protein on their surface. The binding partner can either be expressed naturally on the surface of cells, or be immobilised or in a solution.

The step b) of selection of the complex formed by the binding protein and the binding partner can be performed, as non limitative example, with selective criteria including pH, temperature, solvent, salt concentration, cross reactivity to related binding partners and affinity determined by binding to a low concentration of available binding partner. Binding complexes that do not retain binding proteins to the binding partner in the desired conditions are eliminated.

The step c) of extraction of the sequences encoding the selected binding protein can be performed, as non limitative example, by reinfection of host cells with the selected phage-binding protein complex, cellular amplification and recovery of the vector DNA encoding the selected binding protein.

The step d) of production of the selected binding protein can be performed, as non limitative example, by transformation of the vector into non suppressor bacterial host cells. The Amber stop codon TAG thus being recognised as a stop codon, the binding protein is expressed as a soluble moiety. In another embodiment, it can be achieved by selective cloning of the binding protein into an alternative expression system.

The invention also encompasses the use of the minimized phage display vector of the invention to generate a library of vectors, preferably said use comprising the steps of:

a) inserting the nucleic acid sequences encoding the binding protein in the minimized phage display vector of the invention;

b) transforming a host cell with said phage display vector.

The invention also encompasses the use of the minimized phage display vector of the invention to generate a library of phages, preferably said use comprising the steps of:

a) inserting the nucleic acid sequences encoding the binding protein in the minimized phage display vector of the invention;

b) transforming a host cell with said phage display vector; and c) a step of replication, encapsulation and secretion of phage-binding protein complex by complementation of bacteriophage proteins I-XI.

The invention deals with the use of the minimized phage display vector for the screening of a binding protein specific to a binding partner, preferably said use comprising the steps of:

a) bringing into contact said binding partner with the library of phages according to the invention;

b) selecting the complex formed by the binding protein and the binding partner;

c) extracting the nucleic acid sequences encoding said binding protein from the minimized phage display vector; and d) producing the binding protein.

The invention also comprises a kit containing at least the minimized phage display vector of the invention, specific primers and suppressor cell strains.

By "suppressor cell strains", it is intended to designate a bacterial strain comprising a transfert RNA recognizing a stop codon and inserting an aminio-acid in its place.

As non limitative and preferred examples of such suppressor cell strains, it can be mentioned the suppressor cell strains TG1, XL1-blue, ER2738, ER2267 and HB101.

In a most preferred embodiment of the invention, the specific primers of the kit are selected from the group consisting in the nucleic primers of SEQ ID Nos. 9 to 85.

Other characteristics and advantages of the invention appear further in the description with the examples and figures whose legends are presented below.

FIG. 1: immunoglobulin structure with apparent intra domain loops.

FIG. 2: Amino acid sequences of the constant domain of human Kappa light chains, with the two Cysteine residues in position 27 and 87, respectively, apparent.

FIG. 3: Amino acid sequences of the constant domain of human Lambda light chains, with the two Cysteine residues in position 27 and 86, respectively, apparent.

FIG. 4: Amino acid sequences of human constant domain CH1 of Gamma heavy chains with the two Cysteine residues in position 26 and 82, respectively, apparent.

Figure 5:
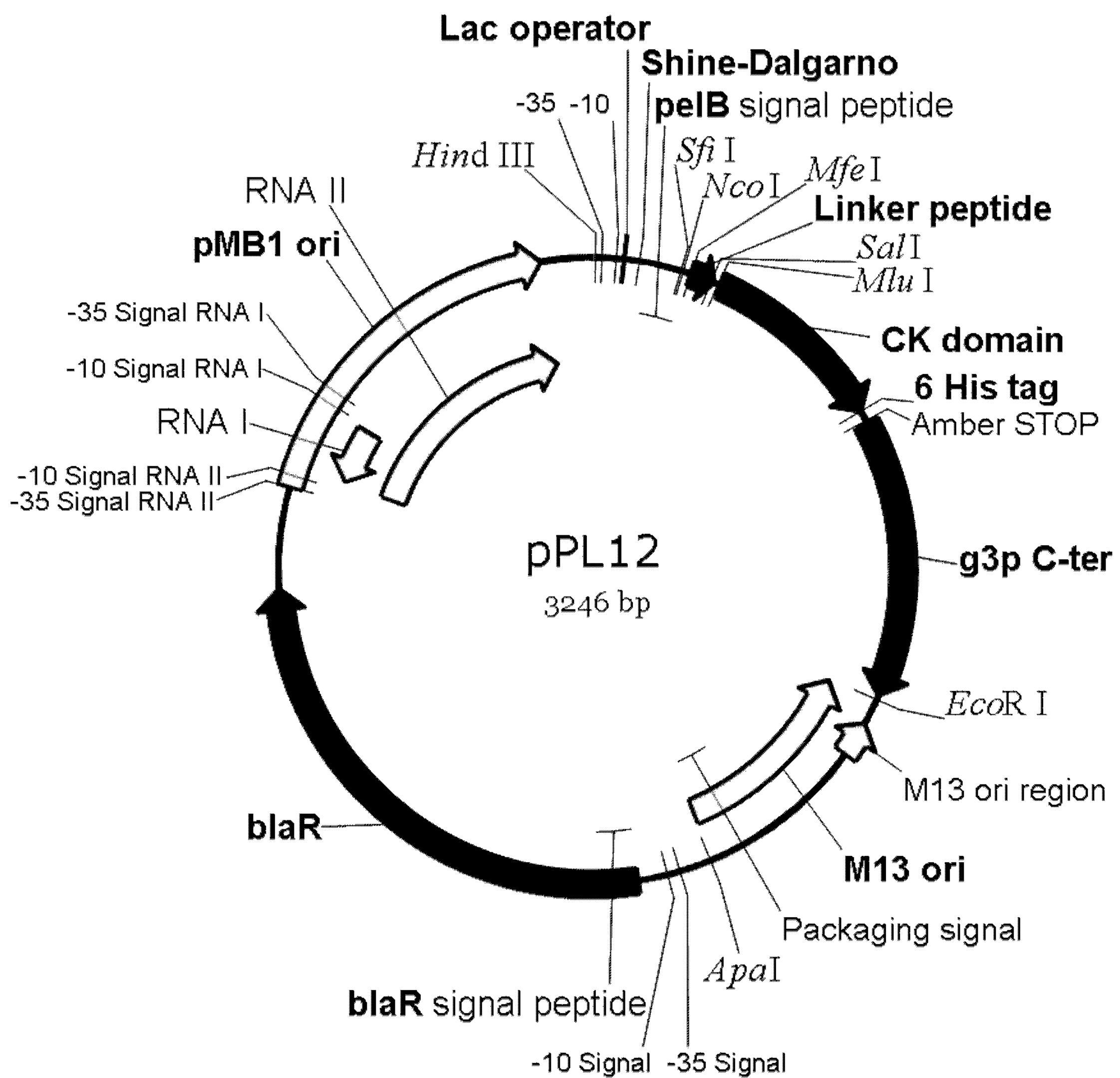

FIG. 5: pPL12 Vector.

Figure 6:
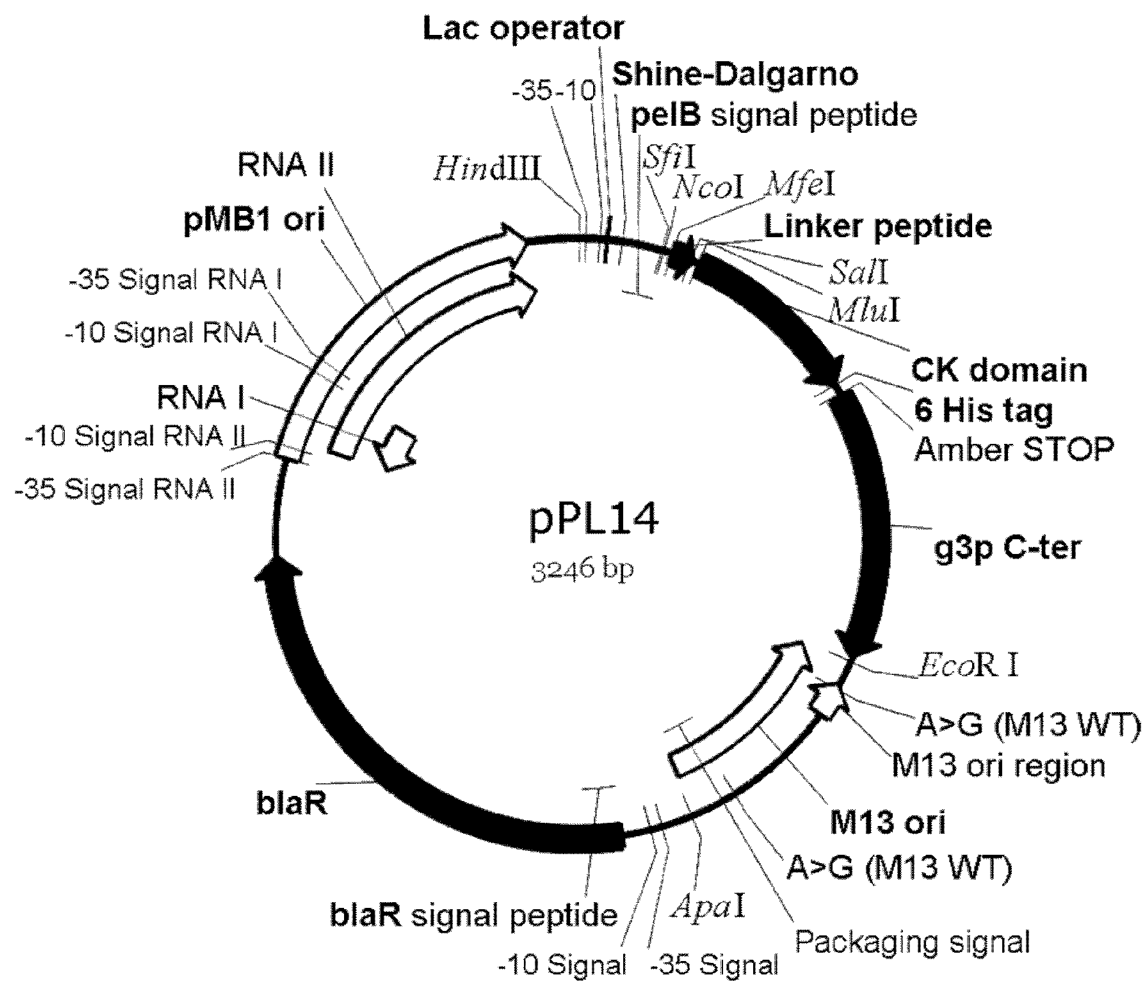

FIG. 6: pPL14 Vector.

Figure 7:
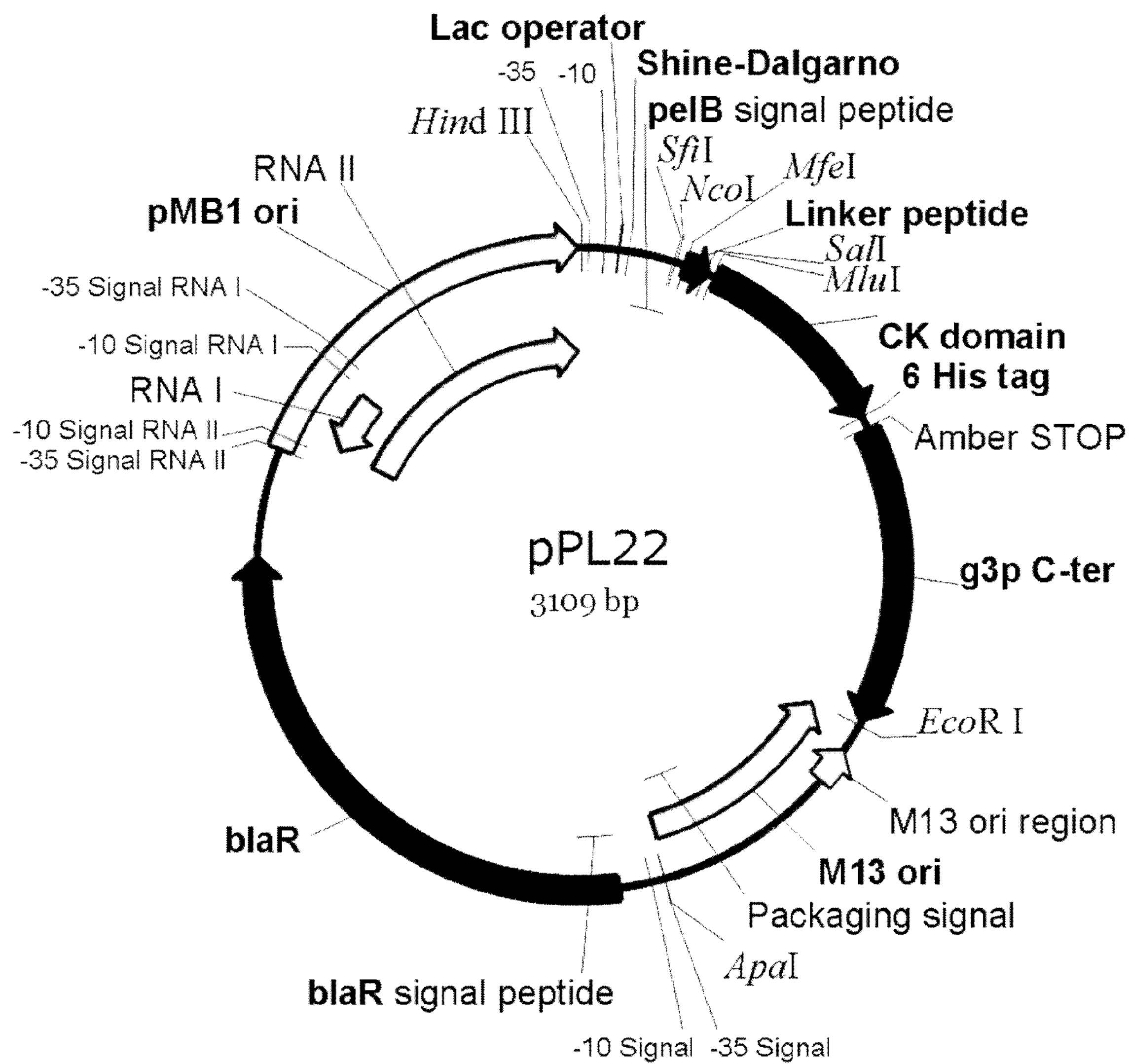

FIG. 7: pPL22 Vector.

Figure 8:
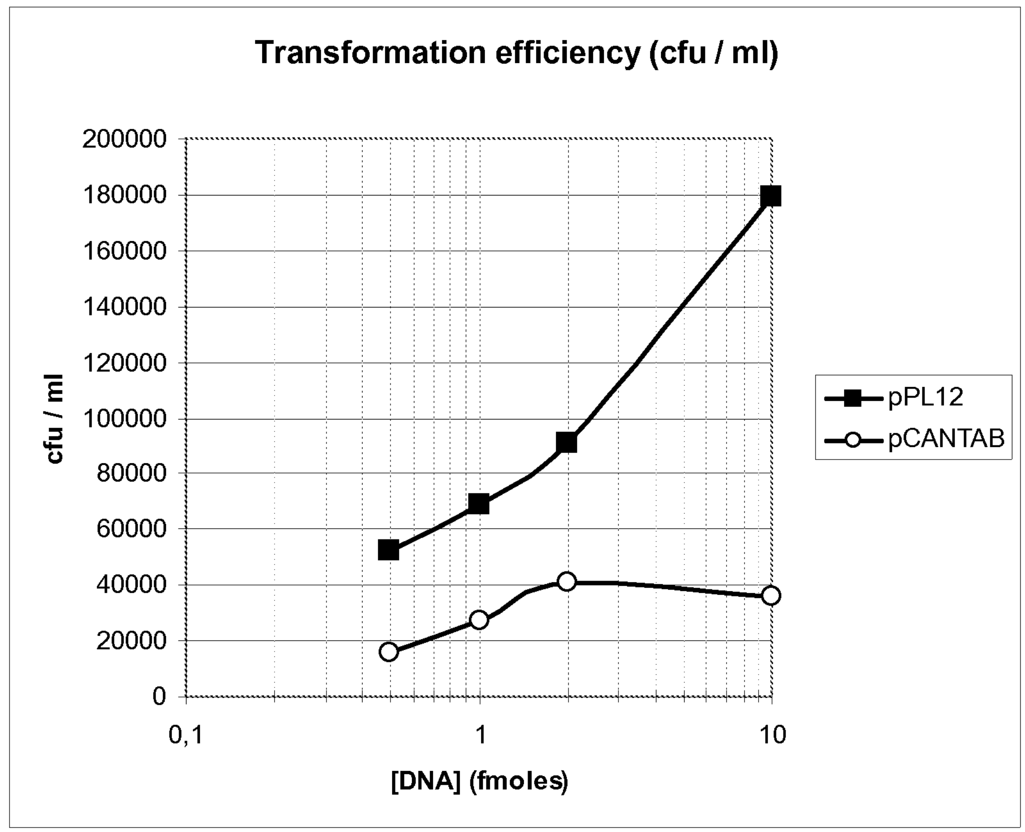

FIG. 8: Transformation efficiency of *Escherichia coli* strain TOP10 (cfu/ml).

Figure 9:
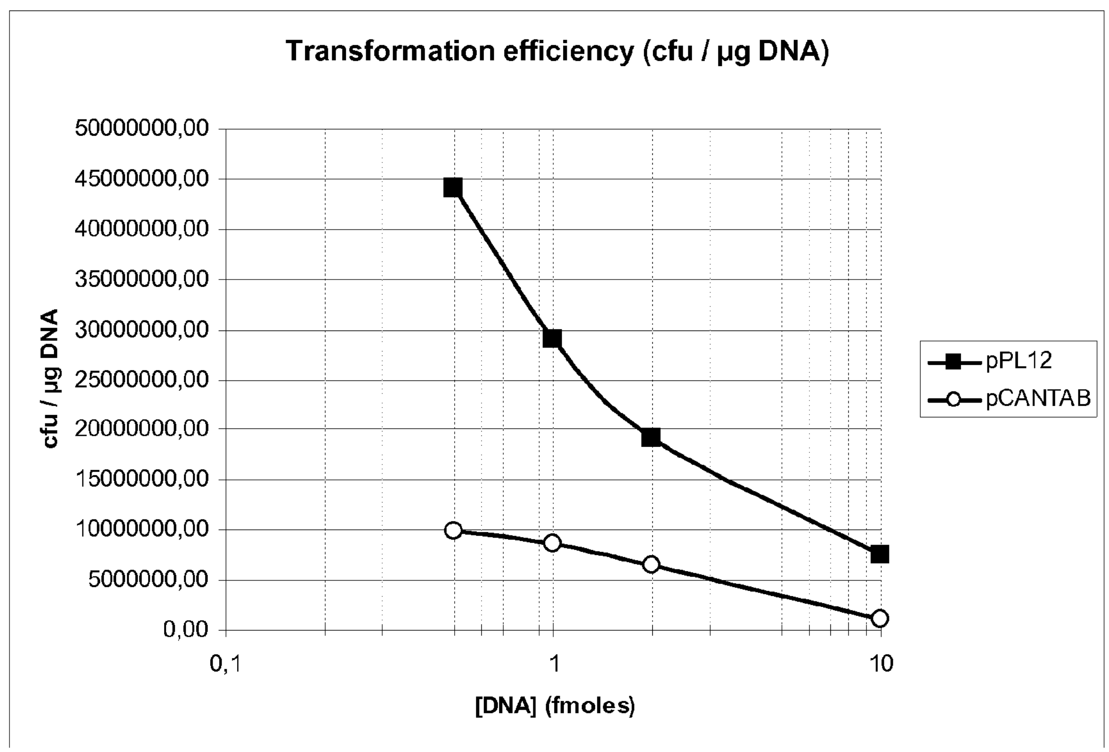

FIG. 9: Transformation efficiency of *Escherichia coli* strain TOP10 (cfu/μg DNA).

Figure 10:
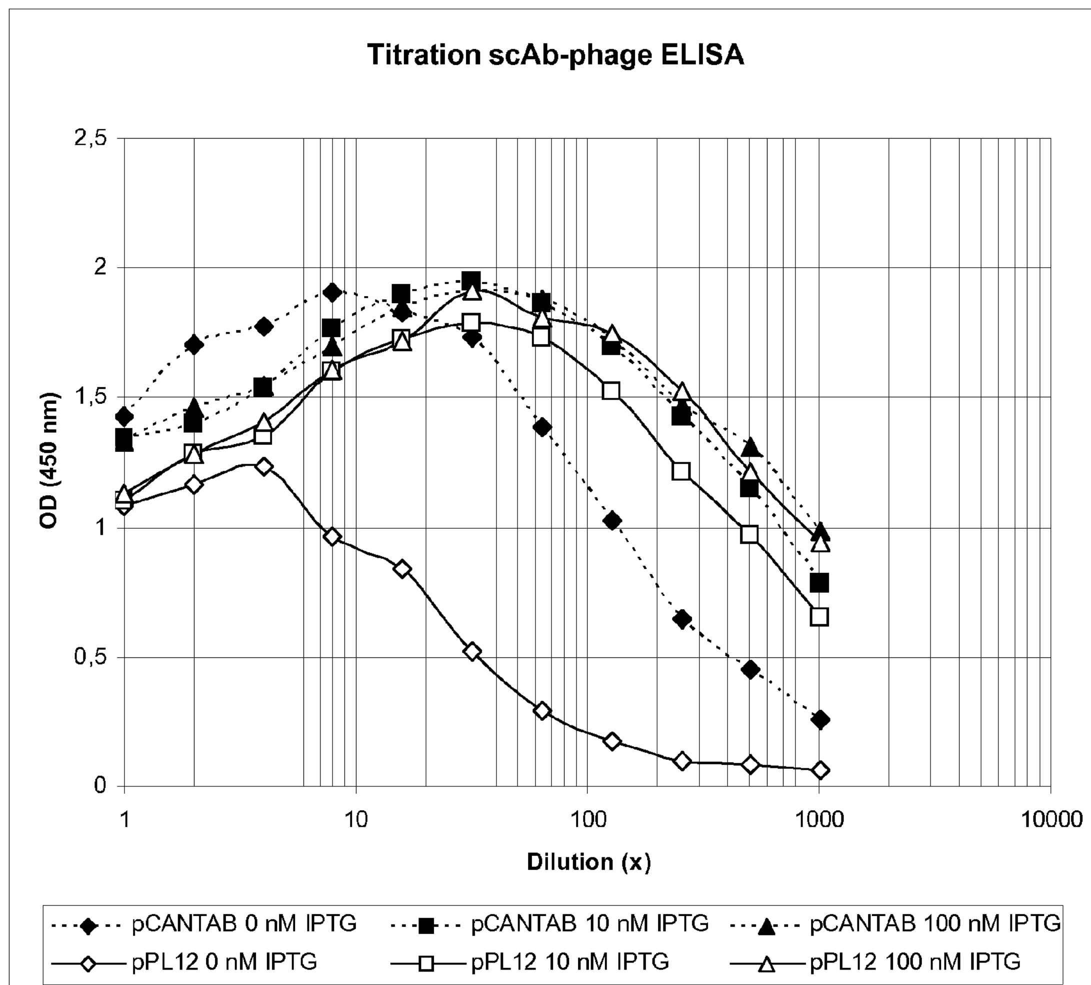

FIG. 10: Effect of IPTG induction upon single chain antibody phage production between pPL12 and pCANTAB.

Figure 11:
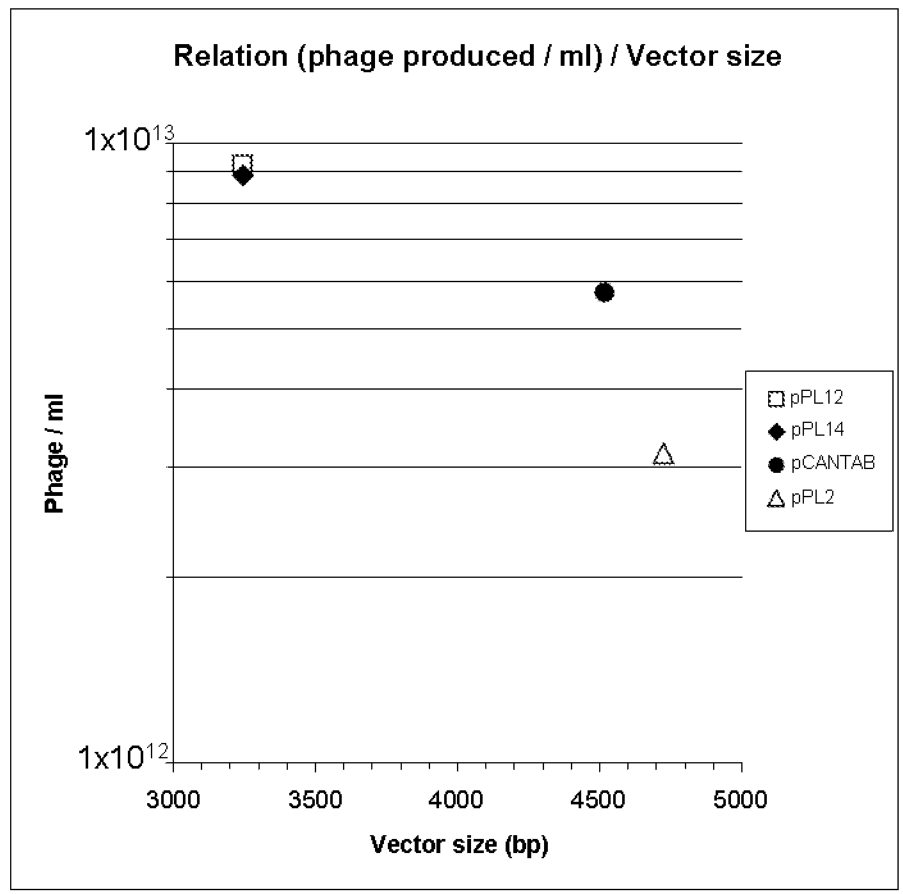

FIG. 11: Relation between phages produced/ml and vector size.

Figure 12:
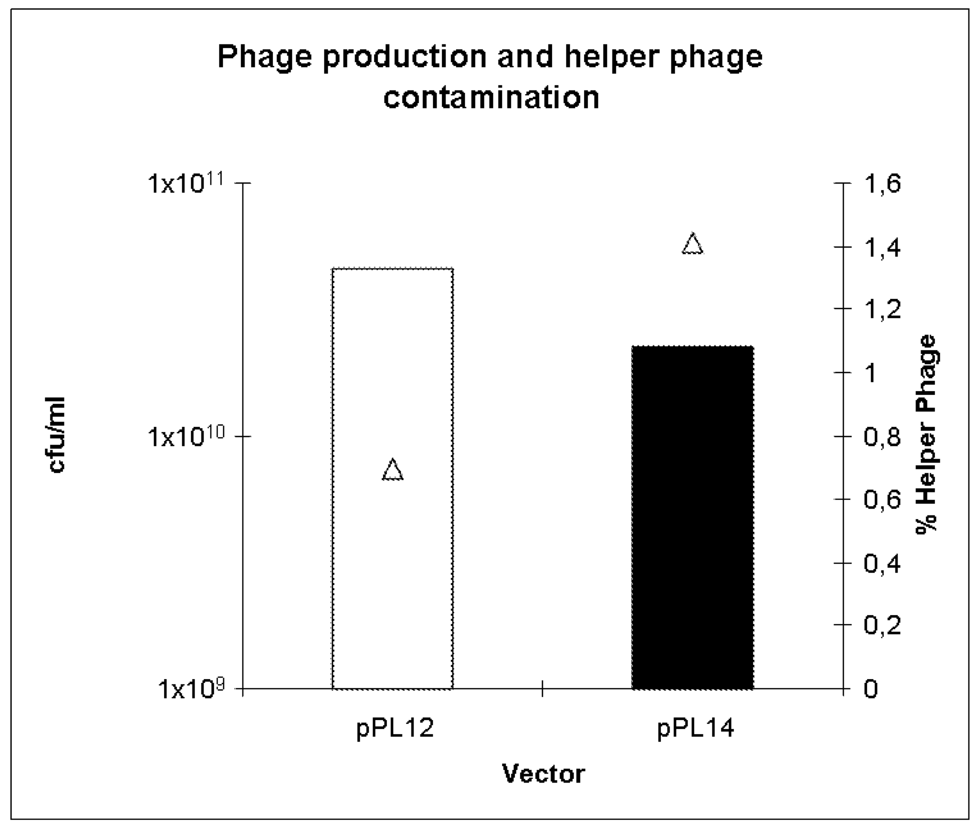

FIG. 12: Comparison of phage production from *Escherichia coli* strain TG1 transformed with the vectors pPL12 and pPL14 and infected with helper phage M13KO7.

Figure 13:
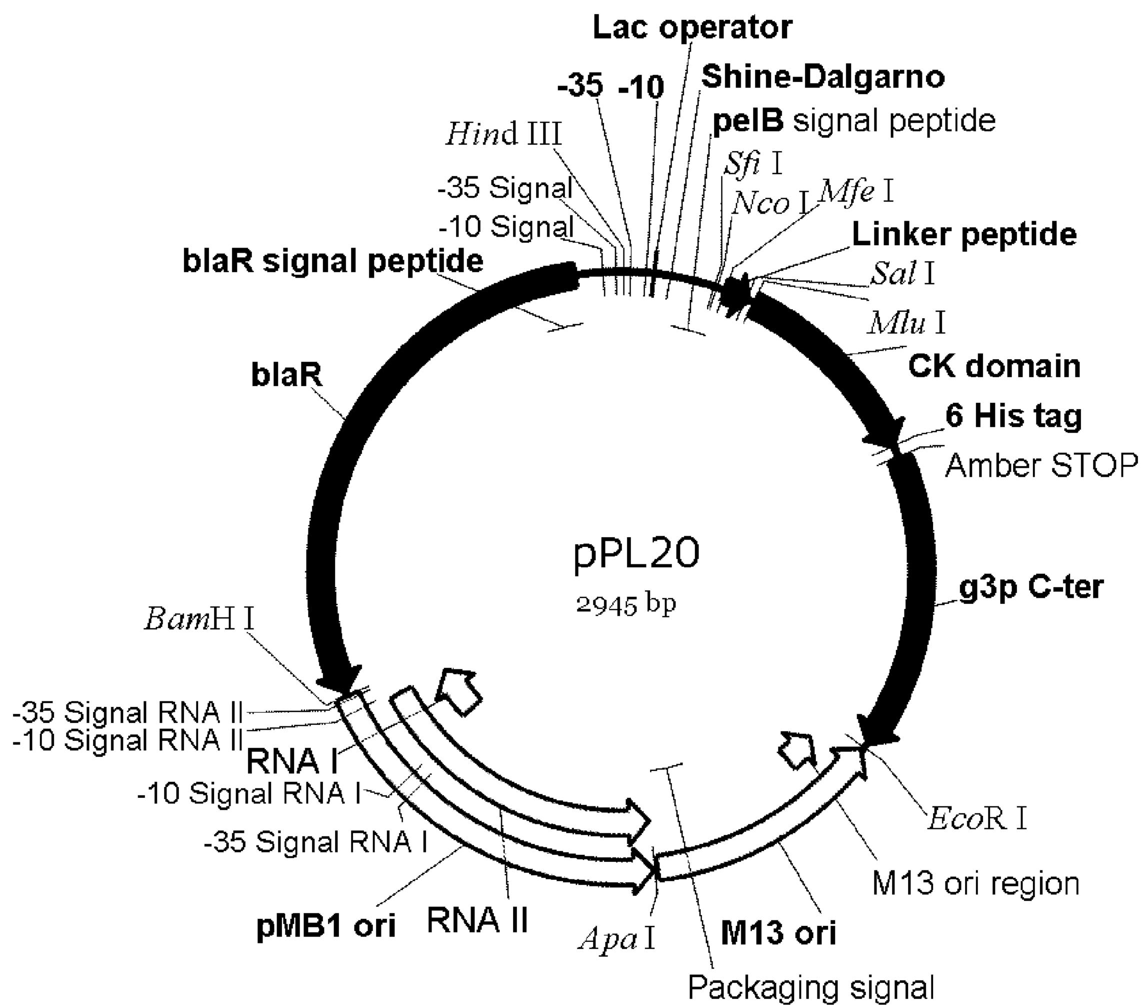

FIG. 13: pPL20 Vector.

Figure 14:
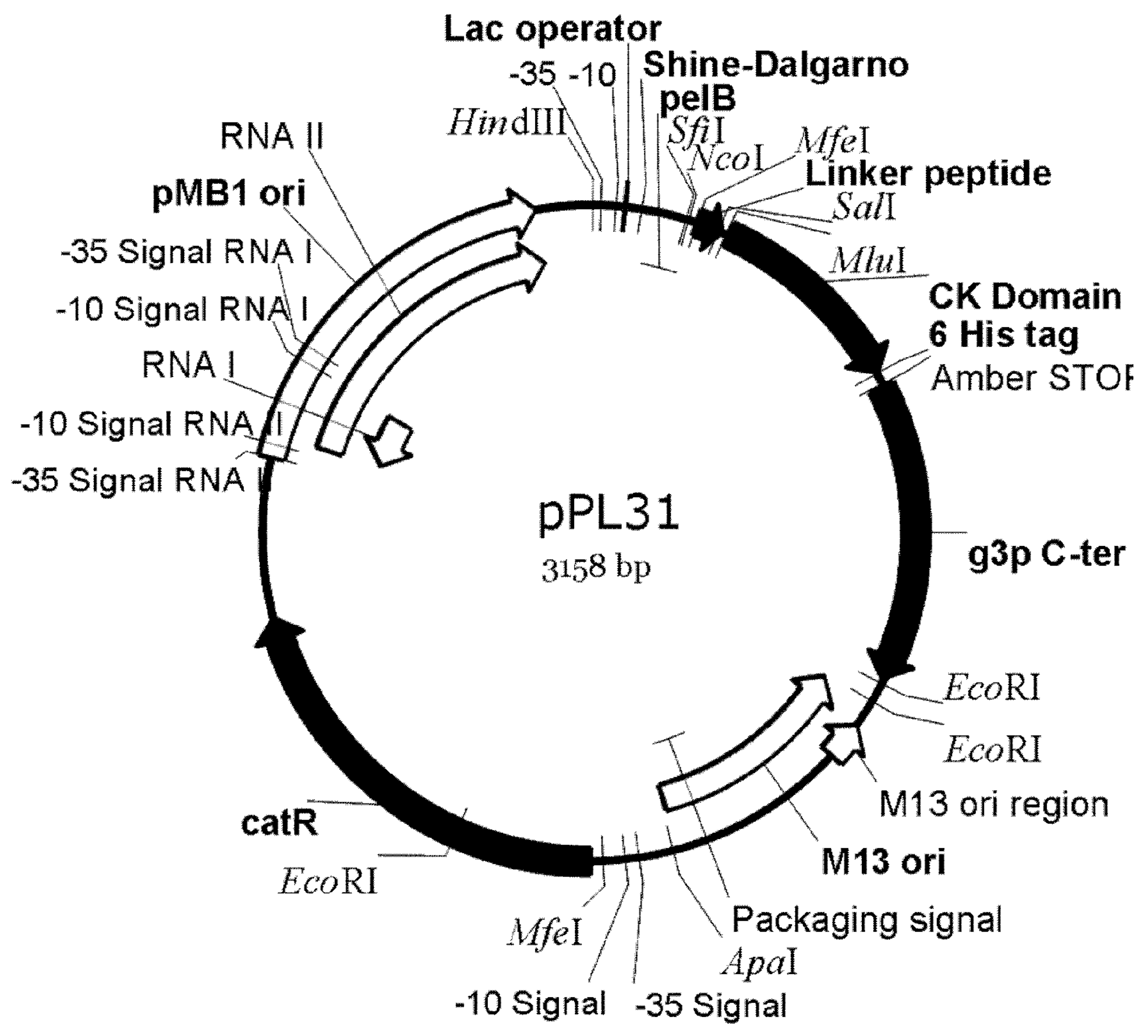

FIG. 14: pPL31 Vector

EXAMPLE 1

Vector Construction

Construction of the vector pPL12 (FIG. 5) was performed through the assembly of synthesised DNA and PCR products following restriction digest of these nucleic acids with relevant restriction enzymes and the ligation of the digestion products.

The cloning cassette comprising the Lac promoter, pelB signal peptide, cloning sites, linking peptide, human kappa 2 constant domain, six histidine tag and amber stop codon was synthesised by Geneart AG (Regensburg, Germany). A Hind III restriction site was included at the 5' extremity to facilitate vector construction. The cloning cassette was synthesised in fusion with the C-terminal domain of the bacteriophage M13 gene III protein, the codon sequences were optimised by Geneart AG for expression in an *E. coli* host. An EcoR I restriction site was introduced during the synthesis at the 3' extremity of the C-terminal domain of the bacteriophage M13 gene III protein following the stop codon. The synthesised DNA fragment consisted of a 1032 bp fragment with Hind III and EcoR I restriction sites at the extremities. Restriction digest of this fragment with Hind III and EcoR I yielded a product of 1026 bp.

The remaining portion of the phage display cassette was amplified by PCR from the phage display vector pCANTAB5E (Amersham lifesciences) using oligonucleotide primers M13oriPSApaI and M13oriPSEcoRI:

```
M13oriPSApaI:
                                        (SEQ ID No. 86)
5'-GGGCCCACGCGCCCTGTAGCGGCGCATTAAG-3'

M13oriPSEcoRI:
                                        (SEQ ID No. 87)
5'-GAATTCCCGAAATCGGCAAAATCCCT-3'
```

The resulting PCR product was a 393 bp fragment with EcoR I and Apa I restriction sites at the extremities. Restriction digest of this fragment with EcoR I and Apa I yielded a product of 391 bp.

The bacterial cassette was amplified by PCR from the cloning vector pUC19 using oligonucleotide primers BlaProApaI and pUCOriHindIII:

```
BlaProApaI:
                                        (SEQ ID No. 88)
5'-GGGCCCACTTTTCGGGGAAATGTGC-3'

pUCOriHindIII:
                                        (SEQ ID No. 89)
5'-AAGCTTATCAGGGGATAACGCAGG-3'
```

The resulting PCR product was a 1835 bp fragment with Apa I and Hind III restriction sites at the extremities. Restriction digest of this fragment with Apa I and Hind III yielded a product of 1829 bp.

The three DNA fragments 1026 bp, 391 bp and 1829 bp were ligated together the orientation being assured by the compatible cohesive ends to generate the vector pPL12 of 3246 bp comprising a cloning cassette (SEQ ID No. 2), a phage display cassette (SEQ ID No. 3) and a bacterial cassette (SEQ ID No. 4).

The ligation product was transformed into *E. coli* cells by heat shock transformation. Resulting positive transformants (resistant to the presence of ampicilin) were selected and the plasmid sequence confirmed by standard DNA sequencing methods.

Vector pPL14 was generated by the site directed mutagenesis of vector pPL12 using oligonucleotide primers M13orilQcS and M13orilQcAS and M13ori2QcS and M13ori2QcAS. Primer couple M13orilQcS and M13orilQcAS introduce the A>G mutation to regenerate the M13 wild type sequence in the M13 packaging signal at position 784 bp in the phage display cassette (SEQ ID No. 6). Primer couple M13ori2QcS and M13ori2QcAS introduce the A>G mutation to regenerate the M13 wild type sequence in the M13 replication origin at position 529 bp in the phage display cassette (SEQ ID No. 6).

```
                                    (SEQ ID No. 139)
M13ori1QcS      CTTGCCAGCGCCCTAGCGCCCGCTCC

                                    (SEQ ID No. 140)
M13ori1QcAS     CTAGGGCGCTGGCAAGTGTAGC

                                    (SEQ ID No. 141)
M13ori2QcS      CAACACTCAACCCTATCTCG

                                    (SEQ ID No. 142)
M13ori2QcAS     AGGGTTGAGTGTTGTTCC
```

Site directed mutagenesis was performed by incubation of 50 ng of the vector pPL12 with first M13orilQcS and M13orilQcAS each at a concentration of 10 μM with 2 μl of dNTP mixture at 10 mM each 5 μl of 10× concentrated reaction buffer for Pfu ultra (Stratagene) and the reaction completed to 50 μl with $H_2O$. Following denaturation of the reaction mixture at 94° C. for 30 s 12 cycles of amplification were performed of 94° C. for 30 seconds followed by 55° C. for 30 seconds and 98° C. for 3 minutes. Following the reaction parent plasmid was removed by treatment with the restriction endonuclease Dpn I. The product of digestion was transformed into *E. coli* cells by heat shock transformation. Resulting positive transformants (resistant to the presence of ampicilin) were selected and the plasmid sequence confirmed by standard DNA sequencing methods. The same procedure was performed on positive clones with the primer couple M13ori2QcS and M 13ori2QcAS to introduce the second mutation. Resulting positive transformants (resistant to the presence of ampicilin) were selected and the plasmid sequence confirmed by standard DNA sequencing methods resulting in the vector pPL14.

Vector pPL22 was generated by the PCR amplification of pPL14 with primers that generated a product that excluded redundant nucleotide sequences in the bacterial cassette. PCR amplification with primers pPL12SenseApaI and pPL12ApaIAS resulted in a PCR product that when treated with the restriction endonuclease Apa I could be religated to generate a product lacking 53 bp between the phage display cassette and the bacterial cassette. The ligation product was transformed into *E. coli* cells by heat shock transformation. Resulting positive transformants were selected and the plasmid sequence confirmed by standard DNA sequencing methods. This material was used as template for PCR amplification with primers Seq1s and pPL12HindIIIAS, the resulting PCR product was treated with the restriction endonuclease Hind III and relegated. The resulting religation product lacked 84 bp between the bacterial cassette and the cloning cassette. The ligation product was transformed into *E. coli* cells by heat shock transformation. Resulting positive transformants were selected and the plasmid sequence confirmed by standard DNA sequencing methods resulting in the vector pPL22 of 3109 bp (SEQ ID No. 7) comprising the novel bacterial cassette (SEQ ID No. 8) containing 134 bp less than the bacterial cassette in pPL12 or 14 (SEQ ID No. 4).

```
pPL12SenseApaI
                                    (SEQ ID No. 143)
GCATGGGCCCTTCAAATATGTATCCGCTCA

pPL12ApaIAS
                                    (SEQ ID No. 144)
GCGCACATTTCCCCGAAAAG

Seq1s
                                    (SEQ ID No. 145)
TTTGCTGGCCTTTTGCTCAC

pPL12HindIIIAS
                                    (SEQ ID No. 146)
GCATAAGCTTTTTCCATAGGCTCCGCCCCCCTGAC
```

EXAMPLE 2

Library Generation

The generation of a library of binding molecules can be performed in the following way.

RNA is extracted from a suitable host, ideally human lymphocytes. The mRNA encoding the desired binding partners is in turn retrotranscribed into cDNA using antisense oligonucleotides complementary to a defined constant region of the desired binding molecules.

The variable regions of the desired binding molecules are in turn amplified by PCR using a panel of sense and antisense oligonucleotides complementary to the 5' and 3' extremities of said variable regions. The sense and antisense oligonucleotides incorporate specific restriction sites for the subsequent cloning of said amplified variable domains. Following restriction digestion of the amplified variable domains with the appropriate restriction enzymes, the resulting DNA fragments can be ligated to the vector of the invention that has in turn been restriction digested with compatible restriction enzymes. The generated compatible restriction site cohesive ends facilitate the directional cloning of binding molecules into the vector of the invention. The resulting ligation product being the vector of the invention and at least one binding molecule is in turn transformed into an appropriate bacterial host.

RNA extraction is preferably performed on isolated B lymphocytes but equally can be performed on isolated mononuclear cells or total non red blood cell population of cells obtained from human blood. Using 1000000 isolated mononuclear cells followed by extraction of total RNA with the RNeasy miniprep (QIAGEN GmbH) sufficient RNA is generated for the generation of a library.

Following total RNA isolation cDNA synthesis is performed with Superscript III reverse transcriptase although other reverse transcriptases can be employed. 2 μg of isolated total RNA is mixed with 2 pmol of a first strand cDNA synthesis primer (SEQ ID Nos. 9, 10 and 11) and 1 μl of dNTPs at a concentration of 10 mM each and the reaction volume completed to 13 μl.

(SEQ ID No. 9)
HuCg 5'-TTGACCAGGCAGCCCAGG-3'

(SEQ ID No. 10)
HuCk 5'-GGAAGATGAAGACAGATGG-3'

(SEQ ID No. 11)
HuCl 5'-ACGGTGCTCCCTTCATGC-3'

The resulting mixture is heated to 65° C. for five minutes before chilling on ice to permit oligonucleotide annealing to the RNA template. Once chilled, 4 μl 5× First-Strand Buffer (250 mM Tris-HCl (pH 8.3 at room temperature), 375 mM KCl, 15 mM $MgCl_2$), 1 μl 0.1 M DTT, 1 μl RNaseOUT™, 1 μl SuperScript™ III RT (200 units/μl) is added and the reaction incubated at 55° C. for one hour. Following heat inactivation of the SuperScript™ enzyme by incubation of the reaction mixture at 70° C. for 15 minutes the resulting cDNA can be used directly as a template for amplification by PCR of binding molecules using the panel of library generation primers. Sense and antisense oligonucleotides are employed as simple pairs or as pools representing either one or both of the sense or antisense orientations of the desired binding molecule. For the amplification of immunoglobulin gamma chain variable domains one or multiple sense oligonucleotides (SEQ ID Nos. 12 to 38) are used in combination with one or more antisense oligonucleotides (SEQ ID Nos. 39 to 45). PCR amplification is performed using Phire® Hot Start DNA polymerase (Finnzymes) although other DNA polymerases can be used in its place. The amplification is performed by preparing a mixture of 1 μl dNTS (10 mM each), sense oligonucleotide or oligonucleotides at a final concentration of 0.5 μM each, antisense oligonucleotide or oligonucleotides at a final concentration of 0.5 μM each, 10 μA 5× Phire™ Reaction buffer, 0.5-1 μl cDNA synthesis product and 1 μA Phire™ Hot Start DNA polymerase. Amplification is performed in an Applied Bio systems 9700 thermal cycler with the following cycling conditions: Initial denaturation 98° C.×30 s, followed by 30 cycles of 98° C.×5 s, 60° C.×5 s and 72° C.×20 s, a final elongation step of 72° C. for 1 min, the reaction then being maintained at 4° C. before storage at −20° C. or exploitation. Amplification of immunoglobulin kappa or lambda chain variable domains is performed in the same fashion replacing the sense oligonucleotides with one or more of the selection SEQ ID Nos. 46 to 58 or 63 to 80 respectively and antisense oligonucleotides SEQ ID 59 to 62 or 81 to 85 respectively.

To improve subsequent restriction digestion, 1 μl of proteinase K (20 mg/ml) can be added to the PCR reaction and incubated at 37° C. for 30 minutes followed by heat inactivation at 70° C. for 15 minutes. This step effectively removes polymerase that remains attached to the extremities of the amplified DNA and may prevent restriction digestion.

Following amplification, the variable domains are treated with a combination of restriction enzymes to facilitate directional cloning into the vector of the invention. The kappa and lambda variable domains and a preparation of the vector of the invention are digested with the restriction endonucleases Sal I and Mlu I. The restriction digested DNA is purified from the unwanted DNA fragments by gel electrophoresis and isolation of the desired DNA fragments with Nucleospin Extract II (Machery Nagel). The resulting purified DNA is then ligated to generate a library of kappa or lambda variable domains in the vector of the invention. The resulting ligation product is then transformed into competent *E. coli* TOP10 cells (Invitrogen) by heat shock transformation. Following heat shock the cells are plated on selective agar plates containing 100 μg/ml ampicilin, thus only cells containing the recombinant vector will survive. The transformed cells represent an immunoglobulin kappa or lambda variable domain library, the presence of stop codons in the vector of the invention preceding the cloned variable domains prevents protein expression and favours vector maintenance.

The transformed cells are recovered from the selective agar plates and the kappa or lambda variable domain library DNA recovered by standard plasmid purification techniques.

The immunoglobulin gamma chain variable domains and the kappa or lambda light chain variable domain libraries present in the vector of the invention are restriction digested with the restriction endonuclease Nco I and Mfe I, with the exception of the Lamda variable domain library generated with HuVL9 (SEQ ID No. 71) that is restriction digested with Sfi I and Mfe I due to the identified presence of Nco I restriction sites in the germline encoded Lambda variable domains amplified with this oligonucleotide. The restriction digested DNA is purified from the unwanted DNA fragments by gel electrophoresis and isolation of the desired DNA fragments with Nucleospin Extract II (Machery Nagel). The resulting purified DNA is then ligated to generate a library of gamma and kappa or lambda variable domains in the vector of the invention. The resulting ligation product is then transformed into competent *E. coli* XL1-Blue, XL1-Blue MFR' or TG1 super competent cells (Stratagene) by electroporation to insure the maximum number of transformants that in turn dictate the diversity of binding molecules present in the generated library. Multiple ligations and transformations can be performed to augment the diversity of the resulting binding molecule library.

The resulting transformants can be utilised immediately to generate phage particles presenting the library of binding molecules by addition of helper phage such as M13KO7 (New England Biolabs) or can be stored at −80° C. with the addition of 20% Glycerol (v/v) and Glucose to a final concentration of 5% (v/v).

EXAMPLE 3

Improved Transformation Efficiency of an Optimised Phage Display Vector

To study the effect of reducing vector size on the efficiency of bacterial host transformation, test transformations were performed of *Escherichia coli* TOP10 heat shock competent cells. Equal numbers of cells were transformed with a range of vector DNA copies from 0.5-10 fmoles. The specific number of vector molecules transformed was considered a more accurate representation of the transformation efficiency as transforming the same DNA concentration results in significantly more copies of a smaller vector being transformed. This we consider would unduly advantage the vector described in the invention.

Cells were incubated on ice with 0.5, 1, 2 or 10 fmoles of either pPL12, or pCANTAB for thirty minutes. A heat shock of 42° C. was applied for precisely 45 seconds. The cells were then chilled on ice for a further 2 minutes. Subsequently the cells were incubated in recovery medium prior to plating on selective agar plates. Following an over night incubation at 37° C. the number of colonies was evaluated.

Transformation efficiency of *Escherichia coli* TOP10 cells by heat shock demonstrated that the transformation of 10 fmoles of pPL12 yields 4.5× more transformants than pCANTAB per ml of cells transformed FIG. 8.

Transformation efficiency per μg of DNA transformed is a common representation and as such was also determined for the purposes of comparison. The transformation efficiency per μg of DNA for vector pPL12 or pCANTAB decreases as the DNA concentration increase from 0.5-10 fmoles. The highest efficiency transformation per μg of DNA is achieved with the lowest DNA concentration (0.5 fmoles), in this condition pPL12 yielded 4.5× more colony forming units (cfu) than pCANTAB (FIG. 9).

EXAMPLE 4

Regulation of Binding Domain Fusion to Phage Particles

To determine the degree of background expression of binding domains fused to phage particles, the heavy and light chain variable domains of an antibody to the oncogene cMET were cloned in cis in the cloning cassette of pPL12 and pCANTAB. The resulting fusion protein being a scFv-Fc fused to the C terminal domain of M13 protein 3 in pPL12 and a scFv fused to the complete protein 3 of bacteriophage M13 in the case of pCANTAB.

*E. coli* TG1 cells harbouring the relevant vectors were incubated in selective growth media to mid log phase ($OD_{600}$ nm 0.6) at which point helper phage M13KO7 was added to the culture at a multiplicity of infection of 20:1. The lac promoter was induced through the addition of the allolactose mimic isopropyl β-D-1-thiogalactopyranoside (IPTG) at a concentration of 0, 10 or 100 nM. Following overnight incubation at 30° C. the produced phage were purified by precipitation and were recovered in phosphate buffered saline (pH 7.4). The obtained phage were subsequently titrated to an immobilised cMET molecule immobilised on a saturated polystyrene 96 well plate at a concentration of 0.7 μg/ml. Following extensive washing, phage that were retained through a functional binding domain fused to all (pCANTAB) or part (pPL12) of the protein 3 were detected by an antibody specific to the protein 8 of the phage coat protein, the antibody being labelled with horse radish peroxidase to facilitate colorimetric detection.

In the absence of IPTG pPL12 displays 3.5× less binding signal than the pCANTAB expressed clone (FIG. 10), indicating a higher level of unrestrained expression from pCANTAB. Induction of binding domain-protein 3 fusion with 10 or 100 nM IPTG yields comparable binding signals from the two expression vectors demonstrating a more tightly controlled but highly inducible protein expression from the pPL12 vector. Lower basal expression favours the maintenance of more toxic clones in a library population and thus is preferred.

EXAMPLE 5

Phage Production in Relation to Vector Size

The effect of vector size on the production of phage from infected *E. coli* host cells was evaluated by comparison of the vectors pPL12 and pPL14 both 3246 bp, pCANTAB of 4522 bp and pPL2 of 4728 bp. The vectors pPL12 and pPL14 differ in only two nucleotide positions in the phage display cassette; pPL2 contains full length M13 protein 3 and the wild type M13 origin or replication and packaging signal but lacks an antibody constant domain.

*E. coli* TG1 cells transformed with the each vector were grown to mid log phase ($OD_{600}$ nm 0.6) in selective growth media and were infected with helper phage M13KO7 at a multiplicity of infection of 20:1. Following overnight growth the produced phage were recovered from the growth medium by precipitation and were in turn titrated prior to infection of mid log phase *E. coli* TG1 cells. The infected cells were plated on selective growth media and the colony forming units (cells infected by phage and expressing the selective growth marker) were enumerated. It was observed that as vector size increased the number of colony forming units obtained demonstrating a lower level of phage production (FIG. 11).

The smallest vectors tested pPL12 and pPL14 both comprising 3246 bp produced $9\times10^{12}$ colony forming units compared to pCANTAB with a size of 4522 bp that produced $5.75\times10^{12}$. The difference in colony forming units produced compares significantly to the difference in vector size, pCANTAB being 1.4× larger than pPL12 producing 1.5× less phage.

EXAMPLE 6

Evaluation of Wild Type or Mutant Residues in the Phage Display Cassette

The effect of mutant or wild type residues in the M13 origin of replication and packaging signal in the phage display cassette of pPL12 was evaluated in comparison to the vector pPL14 that is identical to pPL12 except that it contains the wild type residues in the phage display cassette.

*E. coli* TG1 cells transformed with the vectors pPL12 and pPL14 were grown to mid log phase ($OD_{600}$ nm 0.6) in selective growth media and were infected with helper phage M13KO7 at a multiplicity of infection of 20:1. Following overnight growth the produced phage were recovered from the growth medium by precipitation and were in turn titrated prior to infection of mid log phase *E. coli* TG1 cells. Infected cells were plated on selective growth media containing either the antibiotic ampicilin (100 μg/ml) to select for cells containing the vector or kanamycin (25 μg/ml) to select for cells infected by packaged helper phage M13KO7. The number of colony forming units produced by infection with phage harbouring ampicilin resistance was enumerated (solid bars) and the percentage of contaminating helper phage produced expressed as a percentage (triangles) of this value (FIG. 12).

The vector pPL12 produced 2× more phage particles than pPL14 and contained half the number of contaminating helper phage (0.7% compared to 1.4% for pPL14). The non wild type nucleotides in the M13 origin and packaging signal of the pPL12 phage display cassette are the only differences to pPL14 and account for the increased phage production and reduced helper phage genome encapsulation.

EXAMPLE 7

Limitations of Reduced Size Vector

To further reduce the size of the vector pPL12 elements of the bacterial cassette were amplified by PCR to remove non coding nucleotide regions flanking the selective marker gene blaR and the bacterial origin of replication. The selective marker gene blaR and its constitutive promoter region were amplified from pPL12 with the primers blaRHindIII (SEQ ID No. 134) and blarRBamHI (SEQ ID No. 135) resulting in a 933 by fragment following restriction digestion with the restriction endonucleases Hind III and Bam HI. The bacterial origin of replication pMB1 was amplified from pPL12 with the primers pMB1BamHI (SEQ ID No. 136) and pMBApaI (SEQ ID No. 137) resulting in a 595 bp fragment following restriction digestion with the restriction endonucleases Bam HI and Apa I. Restriction digestion of pPL12 with the restriction endonucleases Hind III and Apa I yielded a fragment of 1417 bp containing the cloning and the phage display cassette. Ligation of the two DNA fragments of 933 bp, 595 bp generated a novel bacterial cassette of 1528 bp (SEQ ID No. 138).

Ligation of the novel bacterial cassette and the 1417 bp fragment from pPL12 yielded the vector pPL20 (SEQ ID No. 147; FIG. 13) of 2945 bp. The restriction sites added to the bacterial origin of replication and the selective marker gene blaR were chosen such that the constitutive expression of the selective marker blaR would not lead to polycistronic read through of inserted binding partners. The ligation product was transformed into *E. coli* cells by heat shock transformation. Numerous transformations of the resulting construction performed on multiple occasions yielded no transformants as opposed to vectors pPL12, pPL14 and pPL22 that upon ligation and transformation repeatedly yielded hundreds of positive clones.

Failure to obtain transformants of the variant pPL20 indicates that limits exist to the non coding regions of the vector that may be expunged. The difference between pPL20 and pPL22 being the 170 bp region between the bacterial origin of replication and the selective marker gene blaR in pPL22 that was replaced by the 6 bp recognition site for the restriction endonuclease Bam HI in pPL20.

EXAMPLE 8

Alternative Positive Selective Marker

The open reading frame for the gene chloramphenicol acetyl transferase (catR) is 201 bp shorter than the beta-lactamase gene. Therefore the size of the vector pPL12 can be reduced by replacing the gene coding for beta-lactamase with the gene coding for chloramphenicol acetyl transferase.

The catR gene was amplified by PCR from the vector pBeloBAC11 (New England Biolabs) with the primers fwCATpPL30FspI and revCATpPL30AhdI. An Fsp I restriction site was introduced in the primer fwCATpPL30FspI (SEQ ID No. 151) and an Ahd I site in the primer revCATpPL30AhdI (SEQ ID No. 152). The vector pPL12 was digested with the restriction enzymes Ssp I and Ahd I. As Fsp I and Ssp I are blunt end cutters the PCR product could be cloned directionally. The sequence was verified by sequencing the catR ORF. An Nco I site present in the catR gene was removed by the introduction of a silent mutation by site directed mutagenesis with the primers FwpPL30NcoICATdel (SEQ ID No. 153) and RevpPL30NcoICATdel (Seq ID No. 154).

The resulting vector pPL31 (SEQ ID No. 148) was tested for the expression of an antibody fragment. Expression levels from pPL31 were comparable to those detected from pPL12.

EXAMPLE 9

Generation of an Artificial Restriction Site

An artificial restriction site was introduced during the construction of the vector pPL31. The said restriction site was generated by introducing two recognition sites for the nicking enzyme Nt.BbvCI on both sense and antisense strands of the vector. The Nt.BbvCI sites were introduced into the vector by PCR amplification of an irrelevant DNA fragment with the primers FwNbBbvCI17Nkan (SEQ ID No. 155) and RevNbBbvCI17Nkan (SEQ ID No. 156). The PCR product was cloned into the Eco RI site in the phage display cassette. Cleavage with Nt.BbvCI and religation of the resulting vector generated the DNA sequence CCTCAGCGTTCAGAGTTATGGCTGAG (SEQ ID No. 157) containing the Nt.BbvCI sites. Incubation of the vector with the enzyme Nt.BbvCI yields two nicks in the opposed DNA strands with single stranded DNA overhangs of 17 bp. The artificial restriction site was verified by sequencing.

The novel artificial restriction site facilitates the highly specific cleavage and reclosing of the vector for subsequent manipulation of isolated clones.

What is claimed is:

1. A minimized phage display vector comprising at least a cloning cassette, a phage display cassette and a bacterial cassette, said minimized phage display vector characterized in that the cloning cassette comprises a nucleic acid sequence encoding a polypeptide corresponding at least to the intra-domain loop of a constant domain of an antibody, said minimized phage display vector having a size of 3300 base pairs or less, said minimized phage display vector characterized in that the cloning cassette comprises at least a nucleic acid sequence encoding a promoter and a nucleic acid sequence encoding a signal peptide, characterized in that said promoter is selected from the group consisting of Lac, Tac, Trp, Tet, T7, SP6, characterized in that said signal peptide is selected from the group consisting of pelB, geneIII, phoA, malE, dsbA, said minimized phage display vector characterized in that the cloning cassette further comprises a nucleic acid sequence encoding a cloning site, said minimized phage display vector characterized in that the phage display cassette comprises a nucleic acid sequence comprising at least the C-terminal domain of M13 gene III protein corresponding to the SEQ ID No 132 or 133, said minimized phage display vector characterized in that the phage display cassette further comprises a nucleic acid sequence encoding a stop codon, a nucleic acid sequence encoding a phage replication origin, and a nucleic acid sequence encoding an encapsulation or packaging sequence, and said minimized phage display vector characterized in that the bacterial cassette comprises at least a nucleic acid sequence encoding a promoter, a nucleic acid sequence encoding a positive selective marker and a nucleic acid sequence encoding a replication origin, characterized in that said promoter is a beta lactamase promoter, characterized in that said positive selective marker is an ampicillin or a chloramphenicol resistance gene.

2. A minimized phage display vector according to claim 1, characterized in that said polypeptide corresponds to the intra-domain loop of a heavy chain constant domain of an antibody.

3. A minimized phage display vector according to claim 1, characterized in that said polypeptide corresponds to a heavy chain constant domain of an antibody.

4. A minimized phage display vector according to claim 3, characterized in that said heavy chain constant domain of an antibody is the CH1 heavy chain constant domain of an antibody.

5. A minimized phage display vector according to claim 1, characterized in that said polypeptide corresponds to the intra-domain loop of a light chain constant domain of an antibody.

6. A minimized phage display vector according to claim 1, characterized in that said polypeptide corresponds to a light chain constant domain of an antibody.

7. A minimized phage display vector according to claim 6, characterized in that said light chain constant domain of an antibody is the light chain Kappa constant domain.

8. A minimized phage display vector according to claim 7, characterized in that the C-terminal cysteine of said light chain Kappa constant domain is deleted.

9. A minimized phage display vector according to claim 6, characterized in that said light chain constant domain of an antibody is a light chain Lambda constant domain.

10. A minimized phage display vector according to claim 1, characterized in that said cloning site comprises at least two restriction sites.

11. A minimized phage display vector according to claim 1, characterized in that said stop codon is an amber stop codon.

12. A minimized phage display vector according to claim 1, characterized in that it consists in pPL12 comprising the nucleic acid sequence SEQ ID No. 1.

13. A minimized phage display vector according to claim 1, characterized in that it consists in pPL14 comprising the nucleic acid sequence SEQ ID No. 5.

14. A minimized phage display vector according to claim 1, characterized in that it consists in pPL22 comprising the nucleic acid sequence SEQ ID No. 7.

15. A minimized phage display vector according to claim 1, characterized in that it consists in pPL31 comprising the nucleic acid sequence SEQ ID No. 148.

16. A Library constituted of minimized phage display vectors according to claim 1.

17. Kit comprising at least the minimized phage display vector according to claim 1, specific primers and suppressor cell strains.

18. Kit according to claim 17, characterized in that said specific primers are selected from the group consisting in the nucleic primers of SEQ ID Nos. 9 to 85.

* * * * *

```
                    SEQUENCE LISTING

<160> NUMBER OF SEQ ID NOS: 157

<210> SEQ ID NO 1
<211> LENGTH: 3246
<212> TYPE: DNA
<213> ORGANISM: artificial sequence
<220> FEATURE:
<223> OTHER INFORMATION: Synthetic construct

<400> SEQUENCE: 1

aagcttccag gctttacact ttatgcttcc ggctcgtata atgtgtggaa ttgtgagcgg     60

ataacaattt cacacaggaa acaggattct atgaaatatc tgctgccgac ggcagcagca    120

ggtctgctgc tgctggcggc ccagccggcc atggcctagt gacaattgaa aagcagcggc    180

agcggtagcg aaagcaagtc gacctgatga acgcgtacgg tggccgctcc cagcgtgttc    240

atcttccccc caagcgacga gcagctgaag agcggcaccg ccagcgtggt gtgtctgctg    300

aacaacttct accccaggga ggccaaggtg cagtggaagg tggacaacgc cctgcagagc    360

ggcaacagcc aggagagcgt caccgagcag gacagcaagg actccaccta cagcctgagc    420

agcaccctga ccctgagcaa ggccgactac gagaagcaca aggtgtacgc ctgtgaggtg    480

acccaccagg gcctgtccag ccccgtgacc aagagcttca acaggggcga gcaccatcat    540
```

```
caccaccatt agggcggttc tggtagcggt gatttcgatt acgaaaaaat ggcgaacgcc    600
aacaaaggtg ccatgaccga aaatgccgat gaaaatgcgc tgcagagcga tgccaaaggt    660
aaactggata gcgttgccac cgattatggt gccgccattg atggctttat tggcgatgtt    720
agcggcctgg cgaatggtaa tggtgccacc ggtgattttg ccggtagcaa tagccagatg    780
gcccaggttg gtgatggtga taacagcccg ctgatgaaca actttcgtca gtatctgccg    840
agcctgccgc agagcgttga atgtcgtccg tttgtgtttg gcgccggcaa accgtacgaa    900
tttagcatcg attgtgataa aatcaacctg ttccgtggcg tttttgcctt tctgctgtac    960
gtggcgacct ttatgtatgt gttcagcacc tttgccaaca tcctgcgcaa caaagaaagc   1020
taataagaat tcccgaaatc ggcaaaatcc cttataaatc aaaagaatag cccgagatag   1080
agttgagtgt tgttccagtt tggaacaaga gtccactatt aaagaacgtg gactccaacg   1140
tcaaagggcg aaaaaccgtc tatcagggcg atggcccact acgtgaacca tcacccaaat   1200
caagtttttt ggggtcgagg tgccgtaaag cactaaatcg gaaccctaaa gggagccccc   1260
gatttagagc ttgacgggga aagccggcga acgtggcgag aaaggaaggg aagaaagcga   1320
aaggagcggg cgctaaggcg ctggcaagtg tagcggtcac gctgcgcgta accaccacac   1380
ccgccgcgct taatgcgccg ctacagggcg cgtgggccca cttttcgggg aaatgtgcgc   1440
ggaaccccta tttgtttatt tttctaaata cattcaaata tgtatccgct catgagacaa   1500
taaccctgat aaatgcttca ataatattga aaaaggaaga gtatgagtat tcaacatttc   1560
cgtgtcgccc ttattccctt ttttgcggca ttttgccttc ctgtttttgc tcacccagaa   1620
acgctggtga aagtaaaaga tgctgaagat cagttgggtg cacgagtggg ttacatcgaa   1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc   1860
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcatttttaa   2460
tttaaaagga tctaggtgaa gatccttttt gataatctca tgaccaaaat cccttaacgt   2520
gagttttcgt tccactgagc gtcagacccc gtagaaaaga tcaaaggatc ttcttgagat   2580
cctttttttc tgcgcgtaat ctgctgcttg caaacaaaaa aaccaccgct accagcggtg   2640
gtttgtttgc cggatcaaga gctaccaact ctttttccga aggtaactgg cttcagcaga   2700
gcgcagatac caaatactgt tcttctagtg tagccgtagt taggccacca cttcaagaac   2760
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacgggggg ttcgtgcaca cagcccagct tggagcgaac gacctacacc   2940
```

-continued

```
gaactgagat acctacagcg tgagctatga gaaagcgcca cgcttcccga agggagaaag   3000

gcggacaggt atccggtaag cggcagggtc ggaacaggag agcgcacgag ggagcttcca   3060

gggggaaacg cctggtatct ttatagtcct gtcgggtttc gccacctctg acttgagcgt   3120

cgatttttgt gatgctcgtc aggggggcgg agcctatgga aaaacgccag caacgcggcc   3180

tttttacggt tcctggcctt ttgctggcct tttgctcaca tgttctttcc tgcgttatcc   3240

cctgat                                                               3246
```

```
<210> SEQ ID NO 2
<211> LENGTH: 552
<212> TYPE: DNA
<213> ORGANISM: artificial sequence
<220> FEATURE:
<223> OTHER INFORMATION: Synthetic construct

<400> SEQUENCE: 2

aagcttccag gctttacact ttatgcttcc ggctcgtata atgtgtggaa ttgtgagcgg     60

ataacaattt cacacaggaa acaggattct atgaaatatc tgctgccgac ggcagcagca    120

ggtctgctgc tgctggcggc ccagccggcc atggcctagt gacaattgaa aagcagcggc    180

agcggtagcg aaagcaagtc gacctgatga acgcgtacgg tggccgctcc cagcgtgttc    240

atcttccccc caagcgacga gcagctgaag agcggcaccg ccagcgtggt gtgtctgctg    300

aacaacttct accccaggga ggccaaggtg cagtggaagg tggacaacgc cctgcagagc    360

ggcaacagcc aggagagcgt caccgagcag gacagcaagg actccaccta cagcctgagc    420

agcaccctga ccctgagcaa ggccgactac gagaagcaca aggtgtacgc ctgtgaggtg    480

acccaccagg gcctgtccag ccccgtgacc aagagcttca acaggggcga gcaccatcat    540

caccaccatt ag                                                        552
```

```
<210> SEQ ID NO 3
<211> LENGTH: 864
<212> TYPE: DNA
<213> ORGANISM: artificial sequence
<220> FEATURE:
<223> OTHER INFORMATION: Synthetic construct

<400> SEQUENCE: 3

ggcggttctg gtagcggtga tttcgattac gaaaaaatgg cgaacgccaa caaaggtgcc     60

atgaccgaaa atgccgatga aaatgcgctg cagagcgatg ccaaaggtaa actggatagc    120

gttgccaccg attatggtgc cgccattgat ggctttattg gcgatgttag cggcctggcg    180

aatggtaatg gtgccaccgg tgattttgcc ggtagcaata gccagatggc ccaggttggt    240

gatggtgata acagcccgct gatgaacaac tttcgtcagt atctgccgag cctgccgcag    300

agcgttgaat gtcgtccgtt tgtgtttggc gccggcaaac cgtacgaatt tagcatcgat    360

tgtgataaaa tcaacctgtt ccgtggcgtt tttgcctttc tgctgtacgt ggcgaccttt    420

atgtatgtgt tcagcacctt tgccaacatc ctgcgcaaca aagaaagcta ataagaattc    480

ccgaaatcgg caaaatccct tataaatcaa aagaatagcc cgagatagag ttgagtgttg    540

ttccagtttg gaacaagagt ccactattaa agaacgtgga ctccaacgtc aaagggcgaa    600

aaaccgtcta tcagggcgat ggcccactac gtgaaccatc acccaaatca agtttttttgg    660

ggtcgaggtg ccgtaaagca ctaaatcgga accctaaagg gagcccccga tttagagctt    720

gacggggaaa gccggcgaac gtggcgagaa aggaagggaa gaaagcgaaa ggagcgggcg    780

ctaaggcgct ggcaagtgta gcggtcacgc tgcgcgtaac caccacaccc gccgcgctta    840
```

atgcgccgct acagggcgcg tggg 864

<210> SEQ ID NO 4
<211> LENGTH: 1830
<212> TYPE: DNA
<213> ORGANISM: artificial sequence
<220> FEATURE:
<223> OTHER INFORMATION: Synthetic construct

<400> SEQUENCE: 4
cccacttttc ggggaaatgt gcgcggaacc cctatttgtt tatttttcta aatacattca 60
aatatgtatc cgctcatgag acaataaccc tgataaatgc ttcaataata ttgaaaaagg 120
aagagtatga gtattcaaca tttccgtgtc gcccttattc ccttttttgc ggcattttgc 180
cttcctgttt ttgctcaccc agaaacgctg gtgaaagtaa aagatgctga agatcagttg 240
ggtgcacgag tgggttacat cgaactggat ctcaacagcg gtaagatcct tgagagtttt 300
cgccccgaag aacgttttcc aatgatgagc acttttaaag ttctgctatg tggcgcggta 360
ttatcccgta ttgacgccgg gcaagagcaa ctcggtcgcc gcatacacta ttctcagaat 420
gacttggttg agtactcacc agtcacagaa aagcatctta cggatggcat gacagtaaga 480
gaattatgca gtgctgccat aaccatgagt gataacactg cggccaactt acttctgaca 540
acgatcggag gaccgaagga gctaaccgct tttttgcaca acatggggga tcatgtaact 600
cgccttgatc gttgggaacc ggagctgaat gaagccatac caaacgacga gcgtgacacc 660
acgatgcctg tagcaatggc aacaacgttg cgcaaactat taactggcga actacttact 720
ctagcttccc ggcaacaatt aatagactgg atggaggcgg ataaagttgc aggaccactt 780
ctgcgctcgg cccttccggc tggctggttt attgctgata aatctggagc cggtgagcgt 840
gggtctcgcg gtatcattgc agcactgggg ccagatggta agccctcccg tatcgtagtt 900
atctacacga cggggagtca ggcaactatg gatgaacgaa atagacagat cgctgagata 960
ggtgcctcac tgattaagca ttggtaactg tcagaccaag tttactcata tatactttag 1020
attgatttaa aacttcattt ttaatttaaa aggatctagg tgaagatcct ttttgataat 1080
ctcatgacca aaatccctta acgtgagttt tcgttccact gagcgtcaga ccccgtagaa 1140
aagatcaaag gatcttcttg agatcctttt tttctgcgcg taatctgctg cttgcaaaca 1200
aaaaaaccac cgctaccagc ggtggtttgt ttgccggatc aagagctacc aactcttttt 1260
ccgaaggtaa ctggcttcag cagagcgcag ataccaaata ctgttcttct agtgtagccg 1320
tagttaggcc accacttcaa gaactctgta gcaccgccta catacctcgc tctgctaatc 1380
ctgttaccag tggctgctgc cagtggcgat aagtcgtgtc ttaccgggtt ggactcaaga 1440
cgatagttac cggataaggc gcagcggtcg ggctgaacgg ggggttcgtg cacacagccc 1500
agcttggagc gaacgaccta caccgaactg agatacctac agcgtgagct atgagaaagc 1560
gccacgcttc ccgaagggag aaaggcggac aggtatccgg taagcggcag ggtcggaaca 1620
ggagagcgca cgagggagct tccaggggga aacgcctggt atctttatag tcctgtcggg 1680
tttcgccacc tctgacttga gcgtcgattt ttgtgatgct cgtcaggggg gcggagccta 1740
tggaaaaacg ccagcaacgc ggccttttta cggttcctgg ccttttgctg gccttttgct 1800
cacatgttct ttcctgcgtt atcccctgat 1830

<210> SEQ ID NO 5
<211> LENGTH: 3246
<212> TYPE: DNA
<213> ORGANISM: artificial sequence
<220> FEATURE:

<223> OTHER INFORMATION: Synthetic construct

<400> SEQUENCE: 5

```
aagcttccag gctttacact ttatgcttcc ggctcgtata atgtgtggaa ttgtgagcgg     60
ataacaattt cacacaggaa acaggattct atgaaatatc tgctgccgac ggcagcagca    120
ggtctgctgc tgctggcggc ccagccggcc atggcctagt gacaattgaa aagcagcggc    180
agcggtagcg aaagcaagtc gacctgatga acgcgtacgg tggccgctcc cagcgtgttc    240
atcttccccc caagcgacga gcagctgaag agcggcaccg ccagcgtggt gtgtctgctg    300
aacaacttct accccaggga ggccaaggtg cagtggaagg tggacaacgc cctgcagagc    360
ggcaacagcc aggagagcgt caccgagcag gacagcaagg actccaccta cagcctgagc    420
agcaccctga ccctgagcaa ggccgactac gagaagcaca aggtgtacgc ctgtgaggtg    480
acccaccagg gcctgtccag ccccgtgacc aagagcttca acaggggcga gcaccatcat    540
caccaccatt agggcggttc tggtagcggt gatttcgatt acgaaaaaat ggcgaacgcc    600
aacaaaggtg ccatgaccga aaatgccgat gaaaatgcgc tgcagagcga tgccaaaggt    660
aaactggata gcgttgccac cgattatggt gccgccattg atggctttat tggcgatgtt    720
agcggcctgg cgaatggtaa tggtgccacc ggtgattttg ccggtagcaa tagccagatg    780
gcccaggttg gtgatggtga taacagcccg ctgatgaaca actttcgtca gtatctgccg    840
agcctgccgc agagcgttga atgtcgtccg tttgtgtttg gcgccggcaa accgtacgaa    900
tttagcatcg attgtgataa aatcaacctg ttccgtggcg tttttgcctt tctgctgtac    960
gtggcgacct ttatgtatgt gttcagcacc tttgccaaca tcctgcgcaa caaagaaagc   1020
taataagaat tcccgaaatc ggcaaaatcc cttataaatc aaaagaatag cccgagatag   1080
ggttgagtgt tgttccagtt tggaacaaga gtccactatt aaagaacgtg gactccaacg   1140
tcaaagggcg aaaaaccgtc tatcagggcg atggcccact acgtgaacca tcacccaaat   1200
caagtttttt ggggtcgagg tgccgtaaag cactaaatcg gaaccctaaa gggagccccc   1260
gatttagagc ttgacgggga aagccggcga acgtggcgag aaaggaaggg aagaaagcga   1320
aaggagcggg cgctagggcg ctggcaagtg tagcggtcac gctgcgcgta accaccacac   1380
ccgccgcgct taatgcgccg ctacagggcg cgtgggccca cttttcgggg aaatgtgcgc   1440
ggaaccccta tttgtttatt tttctaaata cattcaaata tgtatccgct catgagacaa   1500
taaccctgat aaatgcttca ataatattga aaaaggaaga gtatgagtat tcaacatttc   1560
cgtgtcgccc ttattccctt ttttgcggca ttttgccttc ctgtttttgc tcacccagaa   1620
acgctggtga aagtaaaaga tgctgaagat cagttgggtg cacgagtggg ttacatcgaa   1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc   1860
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
```

ctggggccag atggtaagcc ctcccgtatc gtagttatct acacgacggg gagtcaggca 2340
actatggatg aacgaaatag acagatcgct gagataggtg cctcactgat taagcattgg 2400
taactgtcag accaagttta ctcatatata ctttagattg atttaaaact tcatttttaa 2460
tttaaaagga tctaggtgaa gatccttttt gataatctca tgaccaaaat cccttaacgt 2520
gagttttcgt tccactgagc gtcagacccc gtagaaaaga tcaaaggatc ttcttgagat 2580
cctttttttc tgcgcgtaat ctgctgcttg caaacaaaaa aaccaccgct accagcggtg 2640
gtttgtttgc cggatcaaga gctaccaact ctttttccga aggtaactgg cttcagcaga 2700
gcgcagatac caaatactgt tcttctagtg tagccgtagt taggccacca cttcaagaac 2760
tctgtagcac cgcctacata cctcgctctg ctaatcctgt taccagtggc tgctgccagt 2820
ggcgataagt cgtgtcttac cgggttggac tcaagacgat agttaccgga taaggcgcag 2880
cggtcgggct gaacgggggg ttcgtgcaca cagcccagct tggagcgaac gacctacacc 2940
gaactgagat acctacagcg tgagctatga gaaagcgcca cgcttcccga agggagaaag 3000
gcggacaggt atccggtaag cggcagggtc ggaacaggag agcgcacgag ggagcttcca 3060
gggggaaacg cctggtatct ttatagtcct gtcgggtttc gccacctctg acttgagcgt 3120
cgatttttgt gatgctcgtc aggggggcgg agcctatgga aaaacgccag caacgcggcc 3180
tttttacggt tcctggcctt ttgctggcct tttgctcaca tgttctttcc tgcgttatcc 3240
cctgat 3246

<210> SEQ ID NO 6
<211> LENGTH: 864
<212> TYPE: DNA
<213> ORGANISM: artificial sequence
<220> FEATURE:
<223> OTHER INFORMATION: Synthetic construct

<400> SEQUENCE: 6
ggcggttctg gtagcggtga tttcgattac gaaaaaatgg cgaacgccaa caaaggtgcc 60
atgaccgaaa atgccgatga aaatgcgctg cagagcgatg ccaaaggtaa actggatagc 120
gttgccaccg attatggtgc cgccattgat ggctttattg gcgatgttag cggcctggcg 180
aatggtaatg gtgccaccgg tgattttgcc ggtagcaata gccagatggc ccaggttggt 240
gatggtgata acagcccgct gatgaacaac tttcgtcagt atctgccgag cctgccgcag 300
agcgttgaat gtcgtccgtt tgtgtttggc gccggcaaac cgtacgaatt tagcatcgat 360
tgtgataaaa tcaacctgtt ccgtggcgtt tttgcctttc tgctgtacgt ggcgaccttt 420
atgtatgtgt tcagcacctt tgccaacatc ctgcgcaaca aagaaagcta ataagaattc 480
ccgaaatcgg caaaatccct tataaatcaa aagaatagcc cgagataggg ttgagtgttg 540
ttccagtttg gaacaagagt ccactattaa agaacgtgga ctccaacgtc aaagggcgaa 600
aaaccgtcta tcagggcgat ggcccactac gtgaaccatc acccaaatca agttttttgg 660
ggtcgaggtg ccgtaaagca ctaaatcgga accctaaagg gagcccccga tttagagctt 720
gacggggaaa gccggcgaac gtggcgagaa aggaagggaa gaaagcgaaa ggagcgggcg 780
ctagggcgct ggcaagtgta gcggtcacgc tgcgcgtaac caccacaccc gccgcgctta 840
atgcgccgct acagggcgcg tggg 864

<210> SEQ ID NO 7
<211> LENGTH: 3109
<212> TYPE: DNA
<213> ORGANISM: artificial sequence
<220> FEATURE:

<223> OTHER INFORMATION: Synthetic construct

<400> SEQUENCE: 7

```
aagcttccag gctttacact ttatgcttcc ggctcgtata atgtgtggaa ttgtgagcgg     60
ataacaattt cacacaggaa acaggattct atgaaatatc tgctgccgac ggcagcagca    120
ggtctgctgc tgctggcggc ccagccggcc atggcctagt gacaattgaa aagcagcggc    180
agcggtagcg aaagcaagtc gacctgatga acgcgtacgg tggccgctcc cagcgtgttc    240
atcttccccc caagcgacga gcagctgaag agcggcaccg ccagcgtggt gtgtctgctg    300
aacaacttct accccaggga ggccaaggtg cagtggaagg tggacaacgc cctgcagagc    360
ggcaacagcc aggagagcgt caccgagcag gacagcaagg actccaccta cagcctgagc    420
agcaccctga ccctgagcaa ggccgactac gagaagcaca aggtgtacgc ctgtgaggtg    480
acccaccagg gcctgtccag ccccgtgacc aagagcttca acaggggcga gcaccatcat    540
caccaccatt agggcggttc tggtagcggt gatttcgatt acgaaaaaat ggcgaacgcc    600
aacaaaggtg ccatgaccga aaatgccgat gaaaatgcgc tgcagagcga tgccaaaggt    660
aaactggata gcgttgccac cgattatggt gccgccattg atggctttat tggcgatgtt    720
agcggcctgg cgaatggtaa tggtgccacc ggtgattttg ccggtagcaa tagccagatg    780
gcccaggttg gtgatggtga taacagcccg ctgatgaaca actttcgtca gtatctgccg    840
agcctgccgc agagcgttga atgtcgtccg tttgtgtttg gcgccggcaa accgtacgaa    900
tttagcatcg attgtgataa aatcaacctg ttccgtggcg tttttgcctt tctgctgtac    960
gtggcgacct ttatgtatgt gttcagcacc tttgccaaca tcctgcgcaa caaagaaagc   1020
taataagaat tcccgaaatc ggcaaaatcc cttataaatc aaaagaatag cccgagatag   1080
agttgagtgt tgttccagtt tggaacaaga gtccactatt aaagaacgtg gactccaacg   1140
tcaaagggcg aaaaaccgtc tatcagggcg atggcccact acgtgaacca tcacccaaat   1200
caagtttttt ggggtcgagg tgccgtaaag cactaaatcg gaaccctaaa gggagccccc   1260
gatttagagc ttgacgggga aagccggcga acgtggcgag aaaggaaggg aagaaagcga   1320
aaggagcggg cgctaaggcg ctggcaagtg tagcggtcac gctgcgcgta accaccacac   1380
ccgccgcgct taatgcgccg ctacagggcg cgtgggccct tcaaatatgt atccgctcat   1440
gagacaataa ccctgataaa tgcttcaata atattgaaaa aggaagagta tgagtattca   1500
acatttccgt gtcgccctta ttcccttttt tgcggcattt tgccttcctg tttttgctca   1560
cccagaaacg ctggtgaaag taaaagatgc tgaagatcag ttgggtgcac gagtgggtta   1620
catcgaactg gatctcaaca gcggtaagat ccttgagagt tttcgccccg aagaacgttt   1680
tccaatgatg agcactttta aagttctgct atgtggcgcg gtattatccc gtattgacgc   1740
cgggcaagag caactcggtc gccgcataca ctattctcag aatgacttgg ttgagtactc   1800
accagtcaca gaaaagcatc ttacggatgg catgacagta agagaattat gcagtgctgc   1860
cataaccatg agtgataaca ctgcggccaa cttacttctg acaacgatcg gaggaccgaa   1920
ggagctaacc gcttttttgc acaacatggg ggatcatgta actcgccttg atcgttggga   1980
accggagctg aatgaagcca taccaaacga cgagcgtgac accacgatgc ctgtagcaat   2040
ggcaacaacg ttgcgcaaac tattaactgg cgaactactt actctagctt cccggcaaca   2100
attaatagac tggatggagg cggataaagt tgcaggacca cttctgcgct cggcccttcc   2160
ggctggctgg tttattgctg ataaatctgg agccggtgag cgtgggtctc gcggtatcat   2220
tgcagcactg gggccagatg gtaagccctc ccgtatcgta gttatctaca cgacggggag   2280
```

```
tcaggcaact atggatgaac gaaatagaca gatcgctgag ataggtgcct cactgattaa   2340

gcattggtaa ctgtcagacc aagtttactc atatatactt tagattgatt taaaacttca   2400

tttttaattt aaaaggatct aggtgaagat cctttttgat aatctcatga ccaaaatccc   2460

ttaacgtgag ttttcgttcc actgagcgtc agaccccgta gaaaagatca aaggatcttc   2520

ttgagatcct ttttttctgc gcgtaatctg ctgcttgcaa acaaaaaaac caccgctacc   2580

agcggtggtt tgtttgccgg atcaagagct accaactctt tttccgaagg taactggctt   2640

cagcagagcg cagataccaa atactgttct tctagtgtag ccgtagttag gccaccactt   2700

caagaactct gtagcaccgc ctacatacct cgctctgcta atcctgttac cagtggctgc   2760

tgccagtggc gataagtcgt gtcttaccgg gttggactca agacgatagt taccggataa   2820

ggcgcagcgg tcgggctgaa cggggggttc gtgcacacag cccagcttgg agcgaacgac   2880

ctacaccgaa ctgagatacc tacagcgtga gctatgagaa agcgccacgc ttcccgaagg   2940

gagaaaggcg gacaggtatc cggtaagcgg cagggtcgga acaggagagc gcacgaggga   3000

gcttccaggg ggaaacgcct ggtatcttta tagtcctgtc gggtttcgcc acctctgact   3060

tgagcgtcga tttttgtgat gctcgtcagg ggggcggagc ctatggaaa              3109
```

```
<210> SEQ ID NO 8
<211> LENGTH: 1693
<212> TYPE: DNA
<213> ORGANISM: artificial sequence
<220> FEATURE:
<223> OTHER INFORMATION: Synthetic construct

<400> SEQUENCE: 8

cccttcaaat atgtatccgc tcatgagaca ataaccctga taaatgcttc aataatattg     60

aaaaaggaag agtatgagta ttcaacattt ccgtgtcgcc cttattccct tttttgcggc    120

attttgcctt cctgtttttg ctcacccaga aacgctggtg aaagtaaaag atgctgaaga    180

tcagttgggt gcacgagtgg gttacatcga actggatctc aacagcggta agatccttga    240

gagttttcgc cccgaagaac gttttccaat gatgagcact tttaaagttc tgctatgtgg    300

cgcggtatta tcccgtattg acgccgggca agagcaactc ggtcgccgca tacactattc    360

tcagaatgac ttggttgagt actcaccagt cacagaaaag catcttacgg atggcatgac    420

agtaagagaa ttatgcagtg ctgccataac catgagtgat aacactgcgg ccaacttact    480

tctgacaacg atcggaggac cgaaggagct aaccgctttt ttgcacaaca tgggggatca    540

tgtaactcgc cttgatcgtt gggaaccgga gctgaatgaa gccataccaa acgacgagcg    600

tgacaccacg atgcctgtag caatggcaac aacgttgcgc aaactattaa ctggcgaact    660

acttactcta gcttcccggc aacaattaat agactggatg gaggcggata aagttgcagg    720

accacttctg cgctcggccc ttccggctgg ctggtttatt gctgataaat ctggagccgg    780

tgagcgtggg tctcgcggta tcattgcagc actggggcca gatggtaagc cctcccgtat    840

cgtagttatc tacacgacgg ggagtcaggc aactatggat gaacgaaata gacagatcgc    900

tgagataggt gcctcactga ttaagcattg gtaactgtca gaccaagttt actcatatat    960

actttagatt gatttaaaac ttcattttta atttaaaagg atctaggtga agatcctttt   1020

tgataatctc atgaccaaaa tcccttaacg tgagttttcg ttccactgag cgtcagaccc   1080

cgtagaaaag atcaaaggat cttcttgaga tccttttttt ctgcgcgtaa tctgctgctt   1140

gcaaacaaaa aaaccaccgc taccagcggt ggtttgtttg ccggatcaag agctaccaac   1200

tctttttccg aaggtaactg gcttcagcag agcgcagata ccaaatactg ttcttctagt   1260
```

gtagccgtag ttaggccacc acttcaagaa ctctgtagca ccgcctacat acctcgctct 1320
gctaatcctg ttaccagtgg ctgctgccag tggcgataag tcgtgtctta ccgggttgga 1380
ctcaagacga tagttaccgg ataaggcgca gcggtcgggc tgaacggggg gttcgtgcac 1440
acagcccagc ttggagcgaa cgacctacac cgaactgaga tacctacagc gtgagctatg 1500
agaaagcgcc acgcttcccg aagggagaaa ggcggacagg tatccggtaa gcggcagggt 1560
cggaacagga gagcgcacga gggagcttcc agggggaaac gcctggtatc tttatagtcc 1620
tgtcgggttt cgccacctct gacttgagcg tcgatttttg tgatgctcgt caggggggcg 1680
gagcctatgg aaa 1693

<210> SEQ ID NO 9
<211> LENGTH: 18
<212> TYPE: DNA
<213> ORGANISM: artificial sequence
<220> FEATURE:
<223> OTHER INFORMATION: Synthetic primer

<400> SEQUENCE: 9
ttgaccaggc agcccagg 18

<210> SEQ ID NO 10
<211> LENGTH: 19
<212> TYPE: DNA
<213> ORGANISM: artificial sequence
<220> FEATURE:
<223> OTHER INFORMATION: Synthetic primer

<400> SEQUENCE: 10
ggaagatgaa gacagatgg 19

<210> SEQ ID NO 11
<211> LENGTH: 18
<212> TYPE: DNA
<213> ORGANISM: artificial sequence
<220> FEATURE:
<223> OTHER INFORMATION: Synthetic primer

<400> SEQUENCE: 11
acggtgctcc cttcatgc 18

<210> SEQ ID NO 12
<211> LENGTH: 37
<212> TYPE: DNA
<213> ORGANISM: artificial sequence
<220> FEATURE:
<223> OTHER INFORMATION: Synthetic primer

<400> SEQUENCE: 12
agccggccat ggcccaggta cagctgcagc agtcagg 37

<210> SEQ ID NO 13
<211> LENGTH: 35
<212> TYPE: DNA
<213> ORGANISM: artificial sequence
<220> FEATURE:
<223> OTHER INFORMATION: Synthetic primer

<400> SEQUENCE: 13
agccggccat ggcccrgctg cagctgcagg agtcg 35

<210> SEQ ID NO 14
<211> LENGTH: 35
<212> TYPE: DNA

<213> ORGANISM: artificial sequence
<220> FEATURE:
<223> OTHER INFORMATION: Synthetic primer

<400> SEQUENCE: 14
agccggccat ggcccagctg cagctgcagg agtcc 35

<210> SEQ ID NO 15
<211> LENGTH: 35
<212> TYPE: DNA
<213> ORGANISM: artificial sequence
<220> FEATURE:
<223> OTHER INFORMATION: Synthetic primer

<400> SEQUENCE: 15
agccggccat ggcccaggtg cagctacarc agtgg 35

<210> SEQ ID NO 16
<211> LENGTH: 36
<212> TYPE: DNA
<213> ORGANISM: artificial sequence
<220> FEATURE:
<223> OTHER INFORMATION: Synthetic primer

<400> SEQUENCE: 16
agccggccat ggcccaggtg cagctgcagg agttgg 36

<210> SEQ ID NO 17
<211> LENGTH: 35
<212> TYPE: DNA
<213> ORGANISM: Artificial
<220> FEATURE:
<223> OTHER INFORMATION: Synthetic primer

<400> SEQUENCE: 17
agccggccat ggcccaggtg cggctgcagg agtcg 35

<210> SEQ ID NO 18
<211> LENGTH: 35
<212> TYPE: DNA
<213> ORGANISM: artificial sequence
<220> FEATURE:
<223> OTHER INFORMATION: Synthetic primer

<400> SEQUENCE: 18
agccggccat ggcccaggtg cagctgcagg astcg 35

<210> SEQ ID NO 19
<211> LENGTH: 37
<212> TYPE: DNA
<213> ORGANISM: artificial sequence
<220> FEATURE:
<223> OTHER INFORMATION: Synthetic primer

<400> SEQUENCE: 19
agccggccat ggcccaggta cagctggtgg agtctgg 37

<210> SEQ ID NO 20
<211> LENGTH: 37
<212> TYPE: DNA
<213> ORGANISM: artificial sequence
<220> FEATURE:
<223> OTHER INFORMATION: Synthetic primer

<400> SEQUENCE: 20
agccggccat ggcccaggtg cagctgttgg agtctgg 37

<210> SEQ ID NO 21
<211> LENGTH: 37
<212> TYPE: DNA
<213> ORGANISM: artificial sequence
<220> FEATURE:
<223> OTHER INFORMATION: Synthetic primer

<400> SEQUENCE: 21
agccggccat ggcccaggtg cagctggtgg astctgg 37

<210> SEQ ID NO 22
<211> LENGTH: 37
<212> TYPE: DNA
<213> ORGANISM: artificial sequence
<220> FEATURE:
<223> OTHER INFORMATION: Synthetic primer

<400> SEQUENCE: 22
agccggccat ggccgaggtg cagctgttgg agtctgg 37

<210> SEQ ID NO 23
<211> LENGTH: 37
<212> TYPE: DNA
<213> ORGANISM: artificial sequence
<220> FEATURE:
<223> OTHER INFORMATION: Synthetic primer

<400> SEQUENCE: 23
agccggccat ggcccaratg cagctggtgc agtctgg 37

<210> SEQ ID NO 24
<211> LENGTH: 37
<212> TYPE: DNA
<213> ORGANISM: artificial sequence
<220> FEATURE:
<223> OTHER INFORMATION: Synthetic primer

<400> SEQUENCE: 24
agccggccat ggcccaggtg cagctggtgc aatctgg 37

<210> SEQ ID NO 25
<211> LENGTH: 37
<212> TYPE: DNA
<213> ORGANISM: artificial sequence
<220> FEATURE:
<223> OTHER INFORMATION: Synthetic primer

<400> SEQUENCE: 25
agccggccat ggcccaggtk cagctggtgc agtctgg 37

<210> SEQ ID NO 26
<211> LENGTH: 37
<212> TYPE: DNA
<213> ORGANISM: artificial sequence
<220> FEATURE:
<223> OTHER INFORMATION: Synthetic primer

<400> SEQUENCE: 26
agccggccat ggcccaggtc cagcttgtgc agtctgg 37

<210> SEQ ID NO 27
<211> LENGTH: 37
<212> TYPE: DNA
<213> ORGANISM: artificial sequence
<220> FEATURE:
<223> OTHER INFORMATION: Synthetic primer

<400> SEQUENCE: 27
agccggccat ggcccaggtc cagctggtgc artctgg 37

<210> SEQ ID NO 28
<211> LENGTH: 37
<212> TYPE: DNA
<213> ORGANISM: artificial sequence
<220> FEATURE:
<223> OTHER INFORMATION: Synthetic primer

<400> SEQUENCE: 28
agccggccat ggccgaggtc cagctggtac agtctgg 37

<210> SEQ ID NO 29
<211> LENGTH: 37
<212> TYPE: DNA
<213> ORGANISM: artificial sequence
<220> FEATURE:
<223> OTHER INFORMATION: Synthetic primer

<400> SEQUENCE: 29
agccggccat ggccgaggtg cagctggtgc agtctgg 37

<210> SEQ ID NO 30
<211> LENGTH: 35
<212> TYPE: DNA
<213> ORGANISM: artificial sequence
<220> FEATURE:
<223> OTHER INFORMATION: Synthetic primer

<400> SEQUENCE: 30
agccggccat ggccgaagtg cagctggtgc agtcc 35

<210> SEQ ID NO 31
<211> LENGTH: 37
<212> TYPE: DNA
<213> ORGANISM: artificial sequence
<220> FEATURE:
<223> OTHER INFORMATION: Synthetic primer

<400> SEQUENCE: 31
agccggccat ggccgaagtg cagctggtgg agtctgg 37

<210> SEQ ID NO 32
<211> LENGTH: 35
<212> TYPE: DNA
<213> ORGANISM: artificial sequence
<220> FEATURE:
<223> OTHER INFORMATION: Synthetic primer

<400> SEQUENCE: 32
agccggccat ggccgaggtg cagctggtgg agtcc 35

<210> SEQ ID NO 33
<211> LENGTH: 37
<212> TYPE: DNA
<213> ORGANISM: artificial sequence
<220> FEATURE:
<223> OTHER INFORMATION: Synthetic primer

<400> SEQUENCE: 33
agccggccat ggccgaggtg cadctggtgg agtctgg 37

<210> SEQ ID NO 34
<211> LENGTH: 37
<212> TYPE: DNA

<213> ORGANISM: artificial sequence
<220> FEATURE:
<223> OTHER INFORMATION: Synthetic primer

<400> SEQUENCE: 34
agccggccat ggccgaggtg cagctggtgg agactgg 37

<210> SEQ ID NO 35
<211> LENGTH: 37
<212> TYPE: DNA
<213> ORGANISM: artificial sequence
<220> FEATURE:
<223> OTHER INFORMATION: Synthetic primer

<400> SEQUENCE: 35
agccggccat ggccgaggtg cagctggtgg agtctgc 37

<210> SEQ ID NO 36
<211> LENGTH: 37
<212> TYPE: DNA
<213> ORGANISM: artificial sequence
<220> FEATURE:
<223> OTHER INFORMATION: Synthetic primer

<400> SEQUENCE: 36
agccggccat ggccgaggtg cagctggtgg agtctcg 37

<210> SEQ ID NO 37
<211> LENGTH: 37
<212> TYPE: DNA
<213> ORGANISM: artificial sequence
<220> FEATURE:
<223> OTHER INFORMATION: Synthetic primer

<400> SEQUENCE: 37
agccggccat ggcccgggtc accttgaggg agtctgg 37

<210> SEQ ID NO 38
<211> LENGTH: 37
<212> TYPE: DNA
<213> ORGANISM: artificial sequence
<220> FEATURE:
<223> OTHER INFORMATION: Synthetic primer

<400> SEQUENCE: 38
agccggccat ggcccagrtc accttgaagg agtctgg 37

<210> SEQ ID NO 39
<211> LENGTH: 38
<212> TYPE: DNA
<213> ORGANISM: artificial sequence
<220> FEATURE:
<223> OTHER INFORMATION: Synthetic primer

<400> SEQUENCE: 39
gctgcttttc aattgtgagg agacggtgac cgtggtcc 38

<210> SEQ ID NO 40
<211> LENGTH: 38
<212> TYPE: DNA
<213> ORGANISM: artificial sequence
<220> FEATURE:
<223> OTHER INFORMATION: Synthetic primer

<400> SEQUENCE: 40
gctgcttttc aattgtgaag agacggtgac cattgtcc 38

<210> SEQ ID NO 41
<211> LENGTH: 38
<212> TYPE: DNA
<213> ORGANISM: artificial sequence
<220> FEATURE:
<223> OTHER INFORMATION: Synthetic primer

<400> SEQUENCE: 41
gctgcttttc aattgtgagg agacrgtgac cagggtgc 38

<210> SEQ ID NO 42
<211> LENGTH: 39
<212> TYPE: DNA
<213> ORGANISM: artificial sequence
<220> FEATURE:
<223> OTHER INFORMATION: Synthetic primer

<400> SEQUENCE: 42
gctgcttttc aattgtgagg agacggtgac cagggtycc 39

<210> SEQ ID NO 43
<211> LENGTH: 38
<212> TYPE: DNA
<213> ORGANISM: artificial sequence
<220> FEATURE:
<223> OTHER INFORMATION: Synthetic primer

<400> SEQUENCE: 43
gctgcttttc aattgtgagg agacggtgac cagggtcc 38

<210> SEQ ID NO 44
<211> LENGTH: 39
<212> TYPE: DNA
<213> ORGANISM: artificial sequence
<220> FEATURE:
<223> OTHER INFORMATION: Synthetic primer

<400> SEQUENCE: 44
gctgcttttc aattgtgagg agacggtgac cagggttcc 39

<210> SEQ ID NO 45
<211> LENGTH: 37
<212> TYPE: DNA
<213> ORGANISM: artificial sequence
<220> FEATURE:
<223> OTHER INFORMATION: Synthetic primer

<400> SEQUENCE: 45
gctgcttttc aattgtgagg agacrgtgac cagggtg 37

<210> SEQ ID NO 46
<211> LENGTH: 38
<212> TYPE: DNA
<213> ORGANISM: artificial sequence
<220> FEATURE:
<223> OTHER INFORMATION: Synthetic primer

<400> SEQUENCE: 46
gaaagcaagt cgaccgakat tgtgatgacc cagactcc 38

<210> SEQ ID NO 47
<211> LENGTH: 38
<212> TYPE: DNA
<213> ORGANISM: artificial sequence
<220> FEATURE:
<223> OTHER INFORMATION: Synthetic primer

<400> SEQUENCE: 47
gaaagcaagt cgaccgatrt tgtgatgact cagtctcc 38

<210> SEQ ID NO 48
<211> LENGTH: 38
<212> TYPE: DNA
<213> ORGANISM: artificial sequence
<220> FEATURE:
<223> OTHER INFORMATION: Synthetic primer

<400> SEQUENCE: 48
gaaagcaagt cgaccgaaat tgtgttgacr cagtctcc 38

<210> SEQ ID NO 49
<211> LENGTH: 38
<212> TYPE: DNA
<213> ORGANISM: artificial sequence
<220> FEATURE:
<223> OTHER INFORMATION: Synthetic primer

<400> SEQUENCE: 49
gaaagcaagt cgaccgaaac gacactcacg cagtctcc 38

<210> SEQ ID NO 50
<211> LENGTH: 38
<212> TYPE: DNA
<213> ORGANISM: artificial sequence
<220> FEATURE:
<223> OTHER INFORMATION: Synthetic primer

<400> SEQUENCE: 50
gaaagcaagt cgaccgaaat tgtaatgaca cagtctcc 38

<210> SEQ ID NO 51
<211> LENGTH: 38
<212> TYPE: DNA
<213> ORGANISM: artificial sequence
<220> FEATURE:
<223> OTHER INFORMATION: Synthetic primer

<400> SEQUENCE: 51
gaaagcaagt cgaccgaaat agtgatgacg cagtctcc 38

<210> SEQ ID NO 52
<211> LENGTH: 38
<212> TYPE: DNA
<213> ORGANISM: artificial sequence
<220> FEATURE:
<223> OTHER INFORMATION: Synthetic primer

<400> SEQUENCE: 52
gaaagcaagt cgaccgacat cgtgatgacc cagtctcc 38

<210> SEQ ID NO 53
<211> LENGTH: 38
<212> TYPE: DNA
<213> ORGANISM: artificial sequence
<220> FEATURE:
<223> OTHER INFORMATION: Synthetic primer

<400> SEQUENCE: 53
gaaagcaagt cgaccgacat ccagatgacc cagtctcc 38

<210> SEQ ID NO 54
<211> LENGTH: 38
<212> TYPE: DNA

<213> ORGANISM: artificial sequence
<220> FEATURE:
<223> OTHER INFORMATION: Synthetic primer

<400> SEQUENCE: 54
gaaagcaagt cgaccgccat ccrgatgacc cagtctcc 38

<210> SEQ ID NO 55
<211> LENGTH: 38
<212> TYPE: DNA
<213> ORGANISM: artificial sequence
<220> FEATURE:
<223> OTHER INFORMATION: Synthetic primer

<400> SEQUENCE: 55
gaaagcaagt cgaccgtcat ctggatgacc cagtctcc 38

<210> SEQ ID NO 56
<211> LENGTH: 38
<212> TYPE: DNA
<213> ORGANISM: artificial sequence
<220> FEATURE:
<223> OTHER INFORMATION: Synthetic primer

<400> SEQUENCE: 56
gaaagcaagt cgaccgmcat ccagttgacc cagtctcc 38

<210> SEQ ID NO 57
<211> LENGTH: 38
<212> TYPE: DNA
<213> ORGANISM: artificial sequence
<220> FEATURE:
<223> OTHER INFORMATION: Synthetic primer

<400> SEQUENCE: 57
gaaagcaagt cgaccracat ccagatgacc cagtctcc 38

<210> SEQ ID NO 58
<211> LENGTH: 38
<212> TYPE: DNA
<213> ORGANISM: artificial sequence
<220> FEATURE:
<223> OTHER INFORMATION: Synthetic primer

<400> SEQUENCE: 58
gaaagcaagt cgaccgatat tgtgatgacc cagactcc 38

<210> SEQ ID NO 59
<211> LENGTH: 29
<212> TYPE: DNA
<213> ORGANISM: artificial sequence
<220> FEATURE:
<223> OTHER INFORMATION: Synthetic primer

<400> SEQUENCE: 59
cgtacgcgtt ttgatctcca ccttggtcc 29

<210> SEQ ID NO 60
<211> LENGTH: 29
<212> TYPE: DNA
<213> ORGANISM: artificial sequence
<220> FEATURE:
<223> OTHER INFORMATION: Synthetic primer

<400> SEQUENCE: 60
cgtacgcgtt ttgatctcca gcttggtcc 29

<210> SEQ ID NO 61
<211> LENGTH: 29
<212> TYPE: DNA
<213> ORGANISM: artificial sequence
<220> FEATURE:
<223> OTHER INFORMATION: Synthetic primer

<400> SEQUENCE: 61
cgtacgcgtt ttgatatcca ctttggtcc 29

<210> SEQ ID NO 62
<211> LENGTH: 29
<212> TYPE: DNA
<213> ORGANISM: artificial sequence
<220> FEATURE:
<223> OTHER INFORMATION: Synthetic primer

<400> SEQUENCE: 62
cgtacgcgtt ttaatctcca gtcgtgtcc 29

<210> SEQ ID NO 63
<211> LENGTH: 34
<212> TYPE: DNA
<213> ORGANISM: artificial sequence
<220> FEATURE:
<223> OTHER INFORMATION: Synthetic primer

<400> SEQUENCE: 63
gaaagcaagt cgacccagtc tgtgctgack cagc 34

<210> SEQ ID NO 64
<211> LENGTH: 34
<212> TYPE: DNA
<213> ORGANISM: artificial sequence
<220> FEATURE:
<223> OTHER INFORMATION: Synthetic primer

<400> SEQUENCE: 64
gaaagcaagt cgacccagtc tgtcgtgacg cagc 34

<210> SEQ ID NO 65
<211> LENGTH: 34
<212> TYPE: DNA
<213> ORGANISM: artificial sequence
<220> FEATURE:
<223> OTHER INFORMATION: Synthetic primer

<400> SEQUENCE: 65
gaaagcaagt cgacccagtc tgtgttgacg cagc 34

<210> SEQ ID NO 66
<211> LENGTH: 34
<212> TYPE: DNA
<213> ORGANISM: artificial sequence
<220> FEATURE:
<223> OTHER INFORMATION: Synthetic primer

<400> SEQUENCE: 66
gaaagcaagt cgacccaggc agggctgact cagc 34

<210> SEQ ID NO 67
<211> LENGTH: 34
<212> TYPE: DNA
<213> ORGANISM: artificial sequence
<220> FEATURE:
<223> OTHER INFORMATION: Synthetic primer

<400> SEQUENCE: 67
gaaagcaagt cgacccagtc tgccctgact cagc 34

<210> SEQ ID NO 68
<211> LENGTH: 34
<212> TYPE: DNA
<213> ORGANISM: artificial sequence
<220> FEATURE:
<223> OTHER INFORMATION: Synthetic primer

<400> SEQUENCE: 68
gaaagcaagt cgacctcttc tgagctgact cagg 34

<210> SEQ ID NO 69
<211> LENGTH: 34
<212> TYPE: DNA
<213> ORGANISM: artificial sequence
<220> FEATURE:
<223> OTHER INFORMATION: Synthetic primer

<400> SEQUENCE: 69
gaaagcaagt cgacctccta tgtgctgact cagc 34

<210> SEQ ID NO 70
<211> LENGTH: 34
<212> TYPE: DNA
<213> ORGANISM: artificial sequence
<220> FEATURE:
<223> OTHER INFORMATION: Synthetic primer

<400> SEQUENCE: 70
gaaagcaagt cgacctccta tgagctgaca cagc 34

<210> SEQ ID NO 71
<211> LENGTH: 34
<212> TYPE: DNA
<213> ORGANISM: artificial sequence
<220> FEATURE:
<223> OTHER INFORMATION: Synthetic primer

<400> SEQUENCE: 71
gaaagcaagt cgacctccta tgagctgatg cagc 34

<210> SEQ ID NO 72
<211> LENGTH: 34
<212> TYPE: DNA
<213> ORGANISM: artificial sequence
<220> FEATURE:
<223> OTHER INFORMATION: Synthetic primer

<400> SEQUENCE: 72
gaaagcaagt cgacctccta tgagctgact cagc 34

<210> SEQ ID NO 73
<211> LENGTH: 34
<212> TYPE: DNA
<213> ORGANISM: artificial sequence
<220> FEATURE:
<223> OTHER INFORMATION: Synthetic primer

<400> SEQUENCE: 73
gaaagcaagt cgaccctgcc tgtgctgact cagc 34

<210> SEQ ID NO 74
<211> LENGTH: 39
<212> TYPE: DNA

<213> ORGANISM: artificial sequence
<220> FEATURE:
<223> OTHER INFORMATION: Synthetic primer

<400> SEQUENCE: 74
gaaagcaagt cgacccagcc tgtgctgact caatcatcc 39

<210> SEQ ID NO 75
<211> LENGTH: 36
<212> TYPE: DNA
<213> ORGANISM: artificial sequence
<220> FEATURE:
<223> OTHER INFORMATION: Synthetic primer

<400> SEQUENCE: 75
gaaagcaagt cgacccagct tgtgctgact caatcg 36

<210> SEQ ID NO 76
<211> LENGTH: 34
<212> TYPE: DNA
<213> ORGANISM: artificial sequence
<220> FEATURE:
<223> OTHER INFORMATION: Synthetic primer

<400> SEQUENCE: 76
gaaagcaagt cgacccagsc tgtgctgact cagc 34

<210> SEQ ID NO 77
<211> LENGTH: 34
<212> TYPE: DNA
<213> ORGANISM: artificial sequence
<220> FEATURE:
<223> OTHER INFORMATION: Synthetic primer

<400> SEQUENCE: 77
gaaagcaagt cgaccaattt tatgctgact cagc 34

<210> SEQ ID NO 78
<211> LENGTH: 34
<212> TYPE: DNA
<213> ORGANISM: artificial sequence
<220> FEATURE:
<223> OTHER INFORMATION: Synthetic primer

<400> SEQUENCE: 78
gaaagcaagt cgacccagrc tgtggtgact cagg 34

<210> SEQ ID NO 79
<211> LENGTH: 34
<212> TYPE: DNA
<213> ORGANISM: artificial sequence
<220> FEATURE:
<223> OTHER INFORMATION: Synthetic primer

<400> SEQUENCE: 79
gaaagcaagt cgacccagac tgtggtgacc cagg 34

<210> SEQ ID NO 80
<211> LENGTH: 34
<212> TYPE: DNA
<213> ORGANISM: artificial sequence
<220> FEATURE:
<223> OTHER INFORMATION: Synthetic primer

<400> SEQUENCE: 80
gaaagcaagt cgacccagcc tgtgctgact cagc 34

<210> SEQ ID NO 81
<211> LENGTH: 30
<212> TYPE: DNA
<213> ORGANISM: artificial sequence
<220> FEATURE:
<223> OTHER INFORMATION: Synthetic primer

<400> SEQUENCE: 81
cgtacgcgtt aggacggtga ccttggtccc 30

<210> SEQ ID NO 82
<211> LENGTH: 30
<212> TYPE: DNA
<213> ORGANISM: artificial sequence
<220> FEATURE:
<223> OTHER INFORMATION: Synthetic primer

<400> SEQUENCE: 82
cgtacgcgtt aggacggtca gcttggtccc 30

<210> SEQ ID NO 83
<211> LENGTH: 30
<212> TYPE: DNA
<213> ORGANISM: artificial sequence
<220> FEATURE:
<223> OTHER INFORMATION: Synthetic primer

<400> SEQUENCE: 83
cgtacgcgtg aggacggtca ccttggtgcc 30

<210> SEQ ID NO 84
<211> LENGTH: 30
<212> TYPE: DNA
<213> ORGANISM: artificial sequence
<220> FEATURE:
<223> OTHER INFORMATION: Synthetic primer

<400> SEQUENCE: 84
cgtacgcgtg aggacggtca gctgggtgcc 30

<210> SEQ ID NO 85
<211> LENGTH: 30
<212> TYPE: DNA
<213> ORGANISM: artificial sequence
<220> FEATURE:
<223> OTHER INFORMATION: Synthetic primer

<400> SEQUENCE: 85
cgtacgcgtg agggcggtca gctgggtgcc 30

<210> SEQ ID NO 86
<211> LENGTH: 31
<212> TYPE: DNA
<213> ORGANISM: artificial sequence
<220> FEATURE:
<223> OTHER INFORMATION: Synthetic primer

<400> SEQUENCE: 86
gggcccacgc gccctgtagc ggcgcattaa g 31

<210> SEQ ID NO 87
<211> LENGTH: 26
<212> TYPE: DNA
<213> ORGANISM: artificial sequence
<220> FEATURE:
<223> OTHER INFORMATION: Synthetic primer

<400> SEQUENCE: 87
gaattcccga aatcggcaaa atccct 26

<210> SEQ ID NO 88
<211> LENGTH: 25
<212> TYPE: DNA
<213> ORGANISM: artificial sequence
<220> FEATURE:
<223> OTHER INFORMATION: Synthetic primer

<400> SEQUENCE: 88
gggcccactt ttcggggaaa tgtgc 25

<210> SEQ ID NO 89
<211> LENGTH: 24
<212> TYPE: DNA
<213> ORGANISM: artificial sequence
<220> FEATURE:
<223> OTHER INFORMATION: Synthetic primer

<400> SEQUENCE: 89
aagcttatca ggggataacg cagg 24

<210> SEQ ID NO 90
<211> LENGTH: 107
<212> TYPE: PRT
<213> ORGANISM: homo sapiens

<400> SEQUENCE: 90

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 91
<211> LENGTH: 107
<212> TYPE: PRT
<213> ORGANISM: homo sapiens

<400> SEQUENCE: 91

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Glu Ser Lys Asp Ser
50 55 60

Thr Tyr Ser Leu Ser Ser Thr Leu Thr Leu Ser Lys Ala Asp Tyr Glu
65 70 75 80

```
Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105


<210> SEQ ID NO 92
<211> LENGTH: 107
<212> TYPE: PRT
<213> ORGANISM: homo sapiens

<400> SEQUENCE: 92

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 93
<211> LENGTH: 107
<212> TYPE: PRT
<213> ORGANISM: homo sapiens

<400> SEQUENCE: 93

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 94
<211> LENGTH: 107
<212> TYPE: PRT
<213> ORGANISM: homo sapiens

<400> SEQUENCE: 94

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 95
<211> LENGTH: 105
<212> TYPE: PRT
<213> ORGANISM: homo sapiens

<400> SEQUENCE: 95

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 96
<211> LENGTH: 105
<212> TYPE: PRT
<213> ORGANISM: homo sapiens

<400> SEQUENCE: 96

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 97
<211> LENGTH: 105
<212> TYPE: PRT
<213> ORGANISM: homo sapiens

<400> SEQUENCE: 97

Gln Pro Lys Ala Ala Pro Ser Val Thr Leu Phe Pro Pro Ser Ser Glu
```

```
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 98
<211> LENGTH: 105
<212> TYPE: PRT
<213> ORGANISM: homo sapiens

<400> SEQUENCE: 98

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Pro Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 99
<211> LENGTH: 105
<212> TYPE: PRT
<213> ORGANISM: homo sapiens

<400> SEQUENCE: 99

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 100
```

```
<211> LENGTH: 105
<212> TYPE: PRT
<213> ORGANISM: homo sapiens

<400> SEQUENCE: 100

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 101
<211> LENGTH: 105
<212> TYPE: PRT
<213> ORGANISM: homo sapiens

<400> SEQUENCE: 101

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Lys Val Ala Trp Lys Ala Asp Gly Ser Pro Val
        35                  40                  45

Asn Thr Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Ala Glu Cys Ser
            100                 105


<210> SEQ ID NO 102
<211> LENGTH: 105
<212> TYPE: PRT
<213> ORGANISM: homo sapiens

<400> SEQUENCE: 102

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Val Ser Asp Phe
            20                  25                  30

Tyr Pro Gly Ala Val Thr Val Ala Trp Lys Ala Asp Gly Ser Pro Val
        35                  40                  45

Lys Val Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Arg Val Thr His Glu Gly Ser Thr Val Glu
```

```
                85                  90                  95

Lys Thr Val Ala Pro Ala Glu Cys Ser
            100                 105


<210> SEQ ID NO 103
<211> LENGTH: 105
<212> TYPE: PRT
<213> ORGANISM: homo sapiens

<400> SEQUENCE: 103

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Val Ser Asp Phe
            20                  25                  30

Tyr Pro Gly Ala Val Thr Val Ala Trp Lys Ala Asp Gly Ser Pro Val
        35                  40                  45

Lys Val Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Arg Val Thr His Glu Gly Ser Thr Val Glu
                85                  90                  95

Lys Thr Val Ala Pro Ala Glu Cys Ser
            100                 105


<210> SEQ ID NO 104
<211> LENGTH: 97
<212> TYPE: PRT
<213> ORGANISM: homo sapiens

<400> SEQUENCE: 104

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val


<210> SEQ ID NO 105
<211> LENGTH: 97
<212> TYPE: PRT
<213> ORGANISM: homo sapiens

<400> SEQUENCE: 105

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
```

```
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val


<210> SEQ ID NO 106
<211> LENGTH: 97
<212> TYPE: PRT
<213> ORGANISM: homo sapiens

<400> SEQUENCE: 106

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val


<210> SEQ ID NO 107
<211> LENGTH: 97
<212> TYPE: PRT
<213> ORGANISM: homo sapiens

<400> SEQUENCE: 107

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Thr Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val


<210> SEQ ID NO 108
<211> LENGTH: 97
<212> TYPE: PRT
<213> ORGANISM: homo sapiens

<400> SEQUENCE: 108

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30
```

```
Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val


<210> SEQ ID NO 109
<211> LENGTH: 97
<212> TYPE: PRT
<213> ORGANISM: homo sapiens

<400> SEQUENCE: 109

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asp His Lys Pro Ser Asn Thr Lys Val Asp Lys Thr
                85                  90                  95

Val


<210> SEQ ID NO 110
<211> LENGTH: 97
<212> TYPE: PRT
<213> ORGANISM: homo sapiens

<400> SEQUENCE: 110

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val


<210> SEQ ID NO 111
<211> LENGTH: 97
<212> TYPE: PRT
<213> ORGANISM: homo sapiens

<400> SEQUENCE: 111

Ser Thr Lys Gly Pro Ser Val Phe Pro Leu Ala Pro Cys Ser Arg Ser
1               5                   10                  15
```

```
Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val


<210> SEQ ID NO 112
<211> LENGTH: 97
<212> TYPE: PRT
<213> ORGANISM: homo sapiens

<400> SEQUENCE: 112

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 113
<211> LENGTH: 97
<212> TYPE: PRT
<213> ORGANISM: homo sapiens

<400> SEQUENCE: 113

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 114
<211> LENGTH: 97
<212> TYPE: PRT
<213> ORGANISM: homo sapiens
```

<400> SEQUENCE: 114

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 115
<211> LENGTH: 97
<212> TYPE: PRT
<213> ORGANISM: homo sapiens

<400> SEQUENCE: 115

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 116
<211> LENGTH: 97
<212> TYPE: PRT
<213> ORGANISM: homo sapiens

<400> SEQUENCE: 116

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 117

<211> LENGTH: 97
<212> TYPE: PRT
<213> ORGANISM: homo sapiens

<400> SEQUENCE: 117

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 118
<211> LENGTH: 97
<212> TYPE: PRT
<213> ORGANISM: homo sapiens

<400> SEQUENCE: 118

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 119
<211> LENGTH: 97
<212> TYPE: PRT
<213> ORGANISM: homo sapiens

<400> SEQUENCE: 119

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95
```

Val

<210> SEQ ID NO 120
<211> LENGTH: 97
<212> TYPE: PRT
<213> ORGANISM: homo sapiens

<400> SEQUENCE: 120

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 121
<211> LENGTH: 97
<212> TYPE: PRT
<213> ORGANISM: homo sapiens

<400> SEQUENCE: 121

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val
```

<210> SEQ ID NO 122
<211> LENGTH: 97
<212> TYPE: PRT
<213> ORGANISM: homo sapiens

<400> SEQUENCE: 122

```
Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80
```

```
Thr Cys Asn Val Asn His Lys Pro Ser Asn Thr Lys Val Asp Lys Arg
                85                  90                  95

Val


<210> SEQ ID NO 123
<211> LENGTH: 97
<212> TYPE: PRT
<213> ORGANISM: homo sapiens

<400> SEQUENCE: 123

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 124
<211> LENGTH: 97
<212> TYPE: PRT
<213> ORGANISM: homo sapiens

<400> SEQUENCE: 124

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 125
<211> LENGTH: 97
<212> TYPE: PRT
<213> ORGANISM: homo sapiens

<400> SEQUENCE: 125

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
```

```
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 126
<211> LENGTH: 97
<212> TYPE: PRT
<213> ORGANISM: homo sapiens

<400> SEQUENCE: 126

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 127
<211> LENGTH: 97
<212> TYPE: PRT
<213> ORGANISM: homo sapiens

<400> SEQUENCE: 127

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 128
<211> LENGTH: 97
<212> TYPE: PRT
<213> ORGANISM: homo sapiens

<400> SEQUENCE: 128

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30
```

```
Pro Glu Pro Val Thr Val Ser Trp Asn Ser Gly Ala Leu Thr Ser Gly
        35                  40                  45

Val His Thr Phe Pro Ala Val Leu Gln Tyr Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 129
<211> LENGTH: 97
<212> TYPE: PRT
<213> ORGANISM: homo sapiens

<400> SEQUENCE: 129

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val


<210> SEQ ID NO 130
<211> LENGTH: 97
<212> TYPE: PRT
<213> ORGANISM: homo sapiens

<400> SEQUENCE: 130

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val


<210> SEQ ID NO 131
<211> LENGTH: 97
<212> TYPE: PRT
<213> ORGANISM: homo sapiens

<400> SEQUENCE: 131

Ser Thr Lys Gly Pro Ser Val Phe Pro Leu Ala Pro Cys Ser Arg Ser
1               5                   10                  15
```

```
Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val


<210> SEQ ID NO 132
<211> LENGTH: 468
<212> TYPE: DNA
<213> ORGANISM: artificial sequence
<220> FEATURE:
<223> OTHER INFORMATION: Synthetic optimized sequence from the M13 gene
      III

<400> SEQUENCE: 132

ggcggttctg gtagcggtga tttcgattac gaaaaaatgg cgaacgccaa caaaggtgcc     60

atgaccgaaa atgccgatga aaatgcgctg cagagcgatg ccaaaggtaa actggatagc    120

gttgccaccg attatggtgc cgccattgat ggctttattg gcgatgttag cggcctggcg    180

aatggtaatg gtgccaccgg tgattttgcc ggtagcaata gccagatggc ccaggttggt    240

gatggtgata acagcccgct gatgaacaac tttcgtcagt atctgccgag cctgccgcag    300

agcgttgaat gtcgtccgtt tgtgtttggc gccggcaaac cgtacgaatt tagcatcgat    360

tgtgataaaa tcaacctgtt ccgtggcgtt tttgcctttc tgctgtacgt ggcgaccttt    420

atgtatgtgt tcagcacctt tgccaacatc ctgcgcaaca aagaaagc                 468


<210> SEQ ID NO 133
<211> LENGTH: 468
<212> TYPE: DNA
<213> ORGANISM: bacteriophage M13

<400> SEQUENCE: 133

ggtggctctg gttccggtga ttttgattat gaaaagatgg caaacgctaa taagggggct     60

atgaccgaaa atgccgatga aaacgcgcta cagtctgacg ctaaaggcaa acttgattct    120

gtcgctactg attacggtgc tgctatcgat ggtttcattg gtgacgtttc cggccttgct    180

aatggtaatg gtgctactgg tgattttgct ggctctaatt cccaaatggc tcaagtcggt    240

gacggtgata attcaccttt aatgaataat ttccgtcaat atttaccttc cctccctcaa    300

tcggttgaat gtcgcccttt tgtctttagc gctggtaaac catatgaatt ttctattgat    360

tgtgacaaaa taaacttatt ccgtggtgtc tttgcgtttc ttttatatgt tgccaccttt    420

atgtatgtat tttctacgtt tgctaacata ctgcgtaata aggagtct                 468


<210> SEQ ID NO 134
<211> LENGTH: 45
<212> TYPE: DNA
<213> ORGANISM: artificial sequence
<220> FEATURE:
<223> OTHER INFORMATION: Synthetic primer

<400> SEQUENCE: 134

tttattaagc ttttcaaata tgtatccgct catgagacaa taacc                     45
```

<210> SEQ ID NO 135
<211> LENGTH: 39
<212> TYPE: DNA
<213> ORGANISM: artificial sequence
<220> FEATURE:
<223> OTHER INFORMATION: Synthetic primer

<400> SEQUENCE: 135
tttattggat ccttaccaat gcttaatcag tgaggcacc 39

<210> SEQ ID NO 136
<211> LENGTH: 43
<212> TYPE: DNA
<213> ORGANISM: artificial sequence
<220> FEATURE:
<223> OTHER INFORMATION: Synthetic primer

<400> SEQUENCE: 136
tttattggat ccttgagatc cttttttct gcgcgtaatc tgc 43

<210> SEQ ID NO 137
<211> LENGTH: 38
<212> TYPE: DNA
<213> ORGANISM: artificial sequence
<220> FEATURE:
<223> OTHER INFORMATION: Synthetic primer

<400> SEQUENCE: 137
tttattgggc cctttccata ggctccgccc ccctgacg 38

<210> SEQ ID NO 138
<211> LENGTH: 1528
<212> TYPE: DNA
<213> ORGANISM: artificial sequence
<220> FEATURE:
<223> OTHER INFORMATION: Synthetic construct

<400> SEQUENCE: 138
ctttccatag gctccgcccc cctgacgagc atcacaaaaa tcgacgctca agtcagaggt 60
ggcgaaaccc gacaggacta taaagatacc aggcgtttcc ccctggaagc tccctcgtgc 120
gctctcctgt tccgaccctg ccgcttaccg gatacctgtc cgcctttctc ccttcgggaa 180
gcgtggcgct ttctcatagc tcacgctgta ggtatctcag ttcggtgtag gtcgttcgct 240
ccaagctggg ctgtgtgcac gaaccccccg ttcagcccga ccgctgcgcc ttatccggta 300
actatcgtct tgagtccaac ccggtaagac acgacttatc gccactggca gcagccactg 360
gtaacaggat tagcagagcg aggtatgtag gcggtgctac agagttcttg aagtggtggc 420
ctaactacgg ctacactaga agaacagtat ttggtatctg cgctctgctg aagccagtta 480
ccttcggaaa aagagttggt agctcttgat ccggcaaaca aaccaccgct ggtagcggtg 540
gtttttttgt ttgcaagcag cagattacgc gcagaaaaaa aggatctcaa ggatccttac 600
caatgcttaa tcagtgaggc acctatctca gcgatctgtc tatttcgttc atccatagtt 660
gcctgactcc ccgtcgtgta gataactacg atacgggagg gcttaccatc tggccccagt 720
gctgcaatga taccgcgaga cccacgctca ccggctccag atttatcagc aataaaccag 780
ccagccggaa gggccgagcg cagaagtggt cctgcaactt tatccgcctc catccagtct 840
attaattgtt gccgggaagc tagagtaagt agttcgccag ttaatagttt gcgcaacgtt 900
gttgccattg ctacaggcat cgtggtgtca cgctcgtcgt ttggtatggc ttcattcagc 960
tccggttccc aacgatcaag gcgagttaca tgatccccca tgttgtgcaa aaaagcggtt 1020
agctccttcg gtcctccgat cgttgtcaga agtaagttgg ccgcagtgtt atcactcatg 1080
gttatggcag cactgcataa ttctcttact gtcatgccat ccgtaagatg cttttctgtg 1140
actggtgagt actcaaccaa gtcattctga gaatagtgta tgcggcgacc gagttgctct 1200
tgcccggcgt caatacggga taataccgcg ccacatagca gaactttaaa agtgctcatc 1260
attggaaaac gttcttcggg gcgaaaactc tcaaggatct taccgctgtt gagatccagt 1320
tcgatgtaac ccactcgtgc acccaactga tcttcagcat cttttacttt caccagcgtt 1380
tctgggtgag caaaaacagg aaggcaaaat gccgcaaaaa agggaataag ggcgacacgg 1440
aaatgttgaa tactcatact cttccttttt caatattatt gaagcattta tcagggttat 1500
tgtctcatga gcggatacat atttgaaa 1528

<210> SEQ ID NO 139
<211> LENGTH: 26
<212> TYPE: DNA
<213> ORGANISM: artificial sequence
<220> FEATURE:
<223> OTHER INFORMATION: Synthetic primer

<400> SEQUENCE: 139
cttgccagcg ccctagcgcc cgctcc 26

<210> SEQ ID NO 140
<211> LENGTH: 22
<212> TYPE: DNA
<213> ORGANISM: artificial sequence
<220> FEATURE:
<223> OTHER INFORMATION: Synthetic primer

<400> SEQUENCE: 140
ctagggcgct ggcaagtgta gc 22

<210> SEQ ID NO 141
<211> LENGTH: 20
<212> TYPE: DNA
<213> ORGANISM: artificial sequence
<220> FEATURE:
<223> OTHER INFORMATION: Synthetic primer

<400> SEQUENCE: 141
caacactcaa ccctatctcg 20

<210> SEQ ID NO 142
<211> LENGTH: 18
<212> TYPE: DNA
<213> ORGANISM: artificial sequence
<220> FEATURE:
<223> OTHER INFORMATION: Synthetic primer

<400> SEQUENCE: 142
agggttgagt gttgttcc 18

<210> SEQ ID NO 143
<211> LENGTH: 30
<212> TYPE: DNA
<213> ORGANISM: artificial sequence
<220> FEATURE:
<223> OTHER INFORMATION: Synthetic primer

<400> SEQUENCE: 143
gcatgggccc ttcaaatatg tatccgctca 30

<210> SEQ ID NO 144
<211> LENGTH: 20
<212> TYPE: DNA
<213> ORGANISM: artificial sequence
<220> FEATURE:
<223> OTHER INFORMATION: Synthetic primer

<400> SEQUENCE: 144
gcgcacattt ccccgaaaag 20

<210> SEQ ID NO 145
<211> LENGTH: 20
<212> TYPE: DNA
<213> ORGANISM: artificial sequence
<220> FEATURE:
<223> OTHER INFORMATION: Synthetic primer

<400> SEQUENCE: 145
tttgctggcc ttttgctcac 20

<210> SEQ ID NO 146
<211> LENGTH: 35
<212> TYPE: DNA
<213> ORGANISM: artificial sequence
<220> FEATURE:
<223> OTHER INFORMATION: Synthetic primer

<400> SEQUENCE: 146
gcataagctt tttccatagg ctccgccccc ctgac 35

<210> SEQ ID NO 147
<211> LENGTH: 2945
<212> TYPE: DNA
<213> ORGANISM: artificial sequence
<220> FEATURE:
<223> OTHER INFORMATION: Synthetic construct

<400> SEQUENCE: 147
agcttccagg ctttacactt tatgcttccg gctcgtataa tgtgtggaat tgtgagcgga 60
taacaatttc acacaggaaa caggattcta tgaaatatct gctgccgacg gcagcagcag 120
gtctgctgct gctggcggcc cagccggcca tggcctagtg acaattgaaa agcagcggca 180
gcggtagcga aagcaagtcg acctgatgaa cgcgtacggt ggccgctccc agcgtgttca 240
tcttcccccc aagcgacgag cagctgaaga gcggcaccgc cagcgtggtg tgtctgctga 300
acaacttcta ccccagggag gccaaggtgc agtggaaggt ggacaacgcc ctgcagagcg 360
gcaacagcca ggagagcgtc accgagcagg acagcaagga ctccacctac agcctgagca 420
gcaccctgac cctgagcaag gccgactacg agaagcacaa ggtgtacgcc tgtgaggtga 480
cccaccaggg cctgtccagc cccgtgacca agagcttcaa caggggcgag caccatcatc 540
accaccatta gggcggttct ggtagcggtg atttcgatta cgaaaaaatg gcgaacgcca 600
acaaaggtgc catgaccgaa aatgccgatg aaaatgcgct gcagagcgat gccaaaggta 660
aactggatag cgttgccacc gattatggtg ccgccattga tggctttatt ggcgatgtta 720
gcggcctggc gaatggtaat ggtgccaccg gtgattttgc cggtagcaat agccagatgg 780
cccaggttgg tgatggtgat aacagcccgc tgatgaacaa ctttcgtcag tatctgccga 840
gcctgccgca gagcgttgaa tgtcgtccgt ttgtgtttgg cgccggcaaa ccgtacgaat 900
ttagcatcga ttgtgataaa atcaacctgt tccgtggcgt ttttgccttt ctgctgtacg 960
tggcgacctt tatgtatgtg ttcagcacct ttgccaacat cctgcgcaac aaagaaagct 1020
aataagaatt cccgaaatcg gcaaaatccc ttataaatca aaagaatagc ccgagataga 1080

```
gttgagtgtt gttccagttt ggaacaagag tccactatta aagaacgtgg actccaacgt   1140

caaagggcga aaaaccgtct atcagggcga tggcccacta cgtgaaccat cacccaaatc   1200

aagttttttg gggtcgaggt gccgtaaagc actaaatcgg aaccctaaag ggagcccccg   1260

atttagagct tgacggggaa agccggcgaa cgtggcgaga aaggaaggga agaaagcgaa   1320

aggagcgggc gctaaggcgc tggcaagtgt agcggtcacg ctgcgcgtaa ccaccacacc   1380

cgccgcgctt aatgcgccgc tacagggcgc gtgggccctt tccataggct ccgccccct    1440

gacgagcatc acaaaaatcg acgctcaagt cagaggtggc gaaacccgac aggactataa   1500

agataccagg cgtttccccc tggaagctcc ctcgtgcgct ctcctgttcc gaccctgccg   1560

cttaccggat acctgtccgc ctttctccct tcgggaagcg tggcgctttc tcatagctca   1620

cgctgtaggt atctcagttc ggtgtaggtc gttcgctcca agctgggctg tgtgcacgaa   1680

ccccccgttc agcccgaccg ctgcgcctta tccggtaact atcgtcttga gtccaacccg   1740

gtaagacacg acttatcgcc actggcagca gccactggta acaggattag cagagcgagg   1800

tatgtaggcg gtgctacaga gttcttgaag tggtggccta actacggcta cactagaaga   1860

acagtatttg gtatctgcgc tctgctgaag ccagttacct tcggaaaaag agttggtagc   1920

tcttgatccg gcaaacaaac caccgctggt agcggtggtt tttttgtttg caagcagcag   1980

attacgcgca gaaaaaaagg atctcaagga tccttaccaa tgcttaatca gtgaggcacc   2040

tatctcagcg atctgtctat ttcgttcatc catagttgcc tgactccccg tcgtgtagat   2100

aactacgata cgggagggct taccatctgg ccccagtgct gcaatgatac cgcgagaccc   2160

acgctcaccg gctccagatt tatcagcaat aaaccagcca gccggaaggg ccgagcgcag   2220

aagtggtcct gcaactttat ccgcctccat ccagtctatt aattgttgcc gggaagctag   2280

agtaagtagt tcgccagtta atagtttgcg caacgttgtt gccattgcta caggcatcgt   2340

ggtgtcacgc tcgtcgtttg gtatggcttc attcagctcc ggttcccaac gatcaaggcg   2400

agttacatga tcccccatgt tgtgcaaaaa agcggttagc tccttcggtc ctccgatcgt   2460

tgtcagaagt aagttggccg cagtgttatc actcatggtt atggcagcac tgcataattc   2520

tcttactgtc atgccatccg taagatgctt ttctgtgact ggtgagtact caaccaagtc   2580

attctgagaa tagtgtatgc ggcgaccgag ttgctcttgc ccggcgtcaa tacgggataa   2640

taccgcgcca catagcagaa ctttaaaagt gctcatcatt ggaaaacgtt cttcggggcg   2700

aaaactctca aggatcttac cgctgttgag atccagttcg atgtaaccca ctcgtgcacc   2760

caactgatct tcagcatctt ttactttcac cagcgtttct gggtgagcaa aaacaggaag   2820

gcaaaatgcc gcaaaaaagg gaataagggc gacacggaaa tgttgaatac tcatactctt   2880

cctttttcaa tattattgaa gcatttatca gggttattgt ctcatgagcg gatacatatt   2940

tgaaa                                                               2945
```

<210> SEQ ID NO 148
<211> LENGTH: 3158
<212> TYPE: DNA
<213> ORGANISM: artificial sequence
<220> FEATURE:
<223> OTHER INFORMATION: Synthetic vector pPL31

<400> SEQUENCE: 148

```
agcttccagg ctttacactt tatgcttccg gctcgtataa tgtgtggaat tgtgagcgga     60

taacaatttc acacaggaaa caggattcta tgaaatatct gctgccgacg gcagcagcag    120

gtctgctgct gctggcggcc cagccggcca tggcctagtg acaattgaaa agcagcggca    180
```

```
gcggtagcga aagcaagtcg acctgatgaa cgcgtacggt ggccgctccc agcgtgttca    240
tcttcccccc aagcgacgag cagctgaaga gcggcaccgc cagcgtggtg tgtctgctga    300
acaacttcta ccccagggag gccaaggtgc agtggaaggt ggacaacgcc ctgcagagcg    360
gcaacagcca ggagagcgtc accgagcagg acagcaagga ctccacctac agcctgagca    420
gcaccctgac cctgagcaag gccgactacg agaagcacaa ggtgtacgcc tgtgaggtga    480
cccaccaggg cctgtccagc cccgtgacca agagcttcaa caggggcgag caccatcatc    540
accaccatta gggcggttct ggtagcggtg atttcgatta cgaaaaaatg gcgaacgcca    600
acaaaggtgc catgaccgaa aatgccgatg aaaatgcgct gcagagcgat gccaaaggta    660
aactggatag cgttgccacc gattatggtg ccgccattga tggctttatt ggcgatgtta    720
gcggcctggc gaatggtaat ggtgccaccg gtgattttgc cggtagcaat agccagatgg    780
cccaggttgg tgatggtgat aacagcccgc tgatgaacaa ctttcgtcag tatctgccga    840
gcctgccgca gagcgttgaa tgtcgtccgt ttgtgtttgg cgccggcaaa ccgtacgaat    900
ttagcatcga ttgtgataaa atcaacctgt tccgtggcgt tttgcctttt ctgctgtacg    960
tggcgacctt tatgtatgtg ttcagcacct ttgccaacat cctgcgcaac aaagaaagct   1020
aataagaatt cctcagcgtt cagagttatg gctgaggaat tcccgaaatc ggcaaaatcc   1080
cttataaatc aaaagaatag cccgagatag agttgagtgt tgttccagtt tggaacaaga   1140
gtccactatt aaagaacgtg gactccaacg tcaaagggcg aaaaaccgtc tatcagggcg   1200
atggcccact acgtgaacca tcacccaaat caagtttttt ggggtcgagg tgccgtaaag   1260
cactaaatcg gaaccctaaa gggagccccc gatttagagc ttgacgggga aagccggcga   1320
acgtggcgag aaaggaaggg aagaaagcga aaggagcggg cgctaaggcg ctggcaagtg   1380
tagcggtcac gctgcgcgta accaccacac ccgccgcgct taatgcgccg ctacagggcg   1440
cgtgggccca cttttcgggg aaatgtgcgc ggaaccccta tttgtttatt tttctaaata   1500
cattcaaata tgtatccgct catgagacaa taaccctgat aaatgcttca ataatgcaat   1560
tgaaaaagga agagtatgga gaaaaaaatc actggatata ccaccgttga tatatcccaa   1620
tggcatcgta aagaacattt tgaggcattt cagtcagttg ctcaatgtac ctataaccag   1680
accgttcagc tggatattac ggccttttta aagaccgtaa agaaaaataa gcacaagttt   1740
tatccggcct ttattcacat tcttgcccgc ctgatgaatg ctcatccgga attccgtatg   1800
gcaatgaaag acggtgagct ggtgatatgg gatagtgttc acccttgtta caccgttttc   1860
catgagcaaa ctgaaacgtt ttcatcgctc tggagtgaat accacgacga tttccggcag   1920
tttctacaca tatattcgca agatgtggcg tgttacggtg aaaacctggc ctatttccct   1980
aaagggttta ttgagaatat gtttttcgtc tcagccaatc cctgggtgag tttcaccagt   2040
tttgatttaa acgtggccaa tatggacaac ttcttcgccc ccgttttcac aatgggcaaa   2100
tattatacgc aaggcgacaa ggtgctgatg ccgctggcga ttcaggttca tcatgccgtt   2160
tgtgatggct tccatgtcgg cagaatgctt aatgaattac aacagtactg cgatgagtgg   2220
cagggcgggg cgtaagacgg ggagtcaggc aactatggat gaacgaaata gacagatcgc   2280
tgagataggt gcctcactga ttaagcattg gtaactgtca gaccaagttt actcatatat   2340
actttagatt gatttaaaac ttcattttta atttaaaagg atctaggtga agatcctttt   2400
tgataatctc atgaccaaaa tcccttaacg tgagttttcg ttccactgag cgtcagaccc   2460
cgtagaaaag atcaaaggat cttcttgaga tccttttttt ctgcgcgtaa tctgctgctt   2520
gcaaacaaaa aaaccaccgc taccagcggt ggtttgtttg ccggatcaag agctaccaac   2580
```

```
tctttttccg aaggtaactg gcttcagcag agcgcagata ccaaatactg ttcttctagt   2640

gtagccgtag ttaggccacc acttcaagaa ctctgtagca ccgcctacat acctcgctct   2700

gctaatcctg ttaccagtgg ctgctgccag tggcgataag tcgtgtctta ccgggttgga   2760

ctcaagacga tagttaccgg ataaggcgca gcggtcgggc tgaacggggg gttcgtgcac   2820

acagcccagc ttggagcgaa cgacctacac cgaactgaga tacctacagc gtgagctatg   2880

agaaagcgcc acgcttcccg aagggagaaa ggcggacagg tatccggtaa gcggcagggt   2940

cggaacagga gagcgcacga gggagcttcc agggggaaac gcctggtatc tttatagtcc   3000

tgtcgggttt cgccacctct gacttgagcg tcgatttttg tgatgctcgt caggggggcg   3060

gagcctatgg aaaaacgcca gcaacgcggc ctttttacgg ttcctggcct tttgctggcc   3120

ttttgctcac atgttctttc ctgcgttatc ccctgata                           3158
```

<210> SEQ ID NO 149
<211> LENGTH: 895
<212> TYPE: DNA
<213> ORGANISM: artificial sequence
<220> FEATURE:
<223> OTHER INFORMATION: Synthetic Phage display cassette of pPL31 vector

<400> SEQUENCE: 149

```
ggcggttctg gtagcggtga tttcgattac gaaaaaatgg cgaacgccaa caaaggtgcc     60

atgaccgaaa atgccgatga aaatgcgctg cagagcgatg ccaaaggtaa actggatagc    120

gttgccaccg attatggtgc cgccattgat ggctttattg gcgatgttag cggcctggcg    180

aatggtaatg gtgccaccgg tgattttgcc ggtagcaata gccagatggc ccaggttggt    240

gatggtgata acagcccgct gatgaacaac tttcgtcagt atctgccgag cctgccgcag    300

agcgttgaat gtcgtccgtt tgtgtttggc gccggcaaac cgtacgaatt tagcatcgat    360

tgtgataaaa tcaacctgtt ccgtggcgtt tttgcctttc tgctgtacgt ggcgaccttt    420

atgtatgtgt tcagcacctt tgccaacatc ctgcgcaaca aagaaagcta ataagaattc    480

ctcagcgttc agagttatgg ctgaggaatt cccgaaatcg gcaaaatccc ttataaatca    540

aaagaatagc ccgagataga gttgagtgtt gttccagttt ggaacaagag tccactatta    600

aagaacgtgg actccaacgt caaagggcga aaaaccgtct atcagggcga tggcccacta    660

cgtgaaccat cacccaaatc aagttttttg gggtcgaggt gccgtaaagc actaaatcgg    720

aaccctaaag ggagcccccg atttagagct tgacggggaa agccggcgaa cgtggcgaga    780

aaggaaggga agaaagcgaa aggagcgggc gctaaggcgc tggcaagtgt agcggtcacg    840

ctgcgcgtaa ccaccacacc cgccgcgctt aatgcgccgc tacagggcgc gtggg         895
```

<210> SEQ ID NO 150
<211> LENGTH: 1711
<212> TYPE: DNA
<213> ORGANISM: artificial sequence
<220> FEATURE:
<223> OTHER INFORMATION: Synthetic Bacterial cassette of pPL31 vector

<400> SEQUENCE: 150

```
cccacttttc ggggaaatgt gcgcggaacc cctatttgtt tatttttcta aatacattca     60

aatatgtatc cgctcatgag acaataaccc tgataaatgc ttcaataatg caattgaaaa    120

aggaagagta tggagaaaaa aatcactgga tataccaccg ttgatatatc ccaatggcat    180

cgtaaagaac attttgaggc atttcagtca gttgctcaat gtacctataa ccagaccgtt    240
```

```
cagctggata ttacggcctt tttaaagacc gtaaagaaaa ataagcacaa gttttatccg    300

gcctttattc acattcttgc ccgcctgatg aatgctcatc cggaattccg tatggcaatg    360

aaagacggtg agctggtgat atgggatagt gttcaccctt gttacaccgt tttccatgag    420

caaactgaaa cgttttcatc gctctggagt gaataccacg acgatttccg gcagtttcta    480

cacatatatt cgcaagatgt ggcgtgttac ggtgaaaacc tggcctattt ccctaaaggg    540

tttattgaga atatgttttt cgtctcagcc aatccctggg tgagtttcac cagttttgat    600

ttaaacgtgg ccaatatgga caacttcttc gcccccgttt tcacaatggg caaatattat    660

acgcaaggcg acaaggtgct gatgccgctg gcgattcagg ttcatcatgc cgtttgtgat    720

ggcttccatg tcggcagaat gcttaatgaa ttacaacagt actgcgatga gtggcagggc    780

ggggcgtaag acggggagtc aggcaactat ggatgaacga aatagacaga tcgctgagat    840

aggtgcctca ctgattaagc attggtaact gtcagaccaa gtttactcat atatacttta    900

gattgattta aaacttcatt tttaatttaa aaggatctag gtgaagatcc tttttgataa    960

tctcatgacc aaaatccctt aacgtgagtt ttcgttccac tgagcgtcag accccgtaga   1020

aaagatcaaa ggatcttctt gagatccttt ttttctgcgc gtaatctgct gcttgcaaac   1080

aaaaaaacca ccgctaccag cggtggtttg tttgccggat caagagctac caactctttt   1140

tccgaaggta actggcttca gcagagcgca gataccaaat actgttcttc tagtgtagcc   1200

gtagttaggc caccacttca agaactctgt agcaccgcct acatacctcg ctctgctaat   1260

cctgttacca gtggctgctg ccagtggcga taagtcgtgt cttaccgggt tggactcaag   1320

acgatagtta ccggataagg cgcagcggtc gggctgaacg gggggttcgt gcacacagcc   1380

cagcttggag cgaacgacct acaccgaact gagataccta cagcgtgagc tatgagaaag   1440

cgccacgctt cccgaaggga gaaaggcgga caggtatccg gtaagcggca gggtcggaac   1500

aggagagcgc acgagggagc ttccaggggg aaacgcctgg tatctttata gtcctgtcgg   1560

gtttcgccac ctctgacttg agcgtcgatt tttgtgatgc tcgtcagggg ggcggagcct   1620

atggaaaaac gccagcaacg cggccttttt acggttcctg gccttttgct ggccttttgc   1680

tcacatgttc tttcctgcgt tatcccctga t                                  1711
```

<210> SEQ ID NO 151
<211> LENGTH: 53
<212> TYPE: DNA
<213> ORGANISM: artificial sequence
<220> FEATURE:
<223> OTHER INFORMATION: Synthetic primer fwCATpPL30FspI

<400> SEQUENCE: 151

```
tgagctgtgc gcaattgaaa aaggaagagt atggagaaaa aaatcactgg ata           53
```

<210> SEQ ID NO 152
<211> LENGTH: 54
<212> TYPE: DNA
<213> ORGANISM: artificial sequence
<220> FEATURE:
<223> OTHER INFORMATION: Synthetic primer revCATpPL30AhdI

<400> SEQUENCE: 152

```
tcgttcatcc atagttgcct gactccccgt cttacgcccc gccctgccac tcat          54
```

<210> SEQ ID NO 153
<211> LENGTH: 36
<212> TYPE: DNA
<213> ORGANISM: artificial sequence
<220> FEATURE:

-continued

```
<223> OTHER INFORMATION: Synthetic primer FwpPL30NcoICATdel

<400> SEQUENCE: 153

cttcgccccc gttttcacaa tgggcaaata ttatac                              36


<210> SEQ ID NO 154
<211> LENGTH: 36
<212> TYPE: DNA
<213> ORGANISM: artificial sequence
<220> FEATURE:
<223> OTHER INFORMATION: Synthetic primer RevpPL30NcoICATdel

<400> SEQUENCE: 154

gtataatatt tgcccattgt gaaaacgggg gcgaag                              36


<210> SEQ ID NO 155
<211> LENGTH: 59
<212> TYPE: DNA
<213> ORGANISM: artificial sequence
<220> FEATURE:
<223> OTHER INFORMATION: Synthetic primer FwNbBbvCI17Nkan

<400> SEQUENCE: 155

agctaataag aattcctcag ccataactct gaacgctgag gttagaaaaa ctcatcgag      59


<210> SEQ ID NO 156
<211> LENGTH: 59
<212> TYPE: DNA
<213> ORGANISM: artificial sequence
<220> FEATURE:
<223> OTHER INFORMATION: Synthetic primer RevNbBbvCI17Nkan

<400> SEQUENCE: 156

agctcgtaag aattcctcag cgttcagagt tatggctgag gaaatttttg ttaaatcag      59


<210> SEQ ID NO 157
<211> LENGTH: 26
<212> TYPE: DNA
<213> ORGANISM: artificial sequence
<220> FEATURE:
<223> OTHER INFORMATION: Synthetic oligonucleotide Nt.BbvCI

<400> SEQUENCE: 157

cctcagcgtt cagagttatg gctgag                                         26
```